(12) United States Patent
Bemis et al.

(10) Patent No.: US 6,368,310 B1
(45) Date of Patent: *Apr. 9, 2002

(54) MEDICAL SUCTION SYSTEM

(75) Inventors: Peter F. Bemis, Sheboygan; Amelia H. Newar, Shorewood; Steven J. Kolste; William J. Genett, both of Sheboygan Falls, all of WI (US)

(73) Assignee: Bemis Manufacturing Company, Sheboygan, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/330,730

(22) Filed: Jun. 11, 1999

Related U.S. Application Data

(63) Continuation of application No. 09/152,632, filed on Sep. 14, 1998, now Pat. No. 5,931,822, which is a continuation of application No. 08/073,108, filed on Jun. 8, 1993, now Pat. No. 5,807,359.

(51) Int. Cl.$^7$ .............................................. A61M 1/00
(52) U.S. Cl. ........................ 604/319; 604/317; 604/322
(58) Field of Search ................................ 604/319, 322, 604/317, 326, 414, 415; 15/339, 302, 304; 422/294, 295, 110, 111

(56) References Cited

U.S. PATENT DOCUMENTS

| | | |
|---|---|---|
| 1,421,325 A | 6/1922 | Walker et al. |
| 1,693,885 A | 12/1928 | Butterworth |
| 1,827,085 A | 10/1931 | Huff |
| 2,004,027 A | 6/1935 | Baxter .......................... 215/74 |
| 2,009,400 A | 7/1935 | Hapgood .................... 226/116 |
| 2,073,746 A | 3/1937 | Keller ........................... 15/14 |
| 2,208,028 A | 7/1940 | Harrington ................. 226/125 |
| 2,438,769 A | 3/1948 | Thomas |
| 2,641,270 A | 6/1953 | Allen |
| 2,799,301 A | 7/1957 | Ballard ........................ 141/317 |
| 2,886,071 A | 5/1959 | Rasmussen .................. 141/82 |
| 3,171,447 A | 3/1965 | Fowler et al. ................ 141/95 |
| 3,363,627 A | 1/1968 | Bidwell et al. ............. 128/276 |
| 3,394,831 A | 7/1968 | Bathish et al. ................ 215/42 |
| 3,482,583 A | 12/1969 | Fenn |
| 3,603,328 A | 9/1971 | Fenn |
| 3,646,935 A | 3/1972 | Holbrook et al. ........... 128/276 |
| 3,671,982 A | 6/1972 | Sayles |
| 3,699,964 A | 10/1972 | Ericson ...................... 128/275 |

(List continued on next page.)

FOREIGN PATENT DOCUMENTS

| | | | |
|---|---|---|---|
| EP | 8602343 | 4/1986 | .................. 15/304 |
| EP | 0596132 A1 | 5/1994 | ........... A01L/11/00 |

OTHER PUBLICATIONS

Judgment in a Civil Case; Bemis Manufacturing Company and Eductor Partnership v. Dornoch Medical Systems, Inc., Case No. 98–C–952; United States District Court, Eastern District of Wisconsin; Decision By Court Dated Aug. 31, 2000.

USPTO, Office Action Summary, Aug. 03, 1999; Application No. 09/193, 455; Applicants, Dunn et al.; Examiner Frankie L. Stinson; Group Art Unit, 1746.

USPTO, Office Action Summary, May 15, 2000; Application No. 09/193,455; Applicants, Dunn et al.; Examiner Frankie L. Stinson; Group Art Unit, 1746.

*Primary Examiner*—John G. Weiss
*Assistant Examiner*—Michele Kidwell
(74) *Attorney, Agent, or Firm*—Michael Best & Friedrich LLP

(57) ABSTRACT

A medical suction system comprising a medical suction canister used in draining bodily fluid from a patient, and a cleaning station for automatically draining and cleaning the suction canister and for automatically providing a visible indication that the canister has been cleaned.

25 Claims, 14 Drawing Sheets

U.S. PATENT DOCUMENTS

| | | | |
|---|---|---|---|
| 3,768,478 A | 10/1973 | Fertik et al. | 128/276 |
| 3,780,757 A | 12/1973 | Jordan | |
| 3,782,414 A | 1/1974 | Holbrook | 137/575 |
| 3,791,394 A | 2/1974 | Hammelmann | |
| 3,863,664 A | 2/1975 | Holbrook et al. | 137/205 |
| 3,866,608 A | 2/1975 | Reynolds et al. | 128/276 |
| 3,897,599 A | 8/1975 | Artzer | |
| 3,916,924 A | 11/1975 | McGowan | 134/95 |
| 3,945,392 A | 3/1976 | Deaton et al. | 137/205 |
| 3,958,730 A | 5/1976 | Caldwell | |
| 3,989,046 A | 11/1976 | Pannier, Jr. et al. | 128/276 |
| 3,995,333 A | 12/1976 | Stephens | |
| 4,004,590 A | 1/1977 | Muriot | 128/276 |
| 4,015,603 A | 4/1977 | Kurtz et al. | 128/276 |
| 4,049,555 A | 9/1977 | Matherne | 210/409 |
| 4,053,284 A | 10/1977 | Posch | 23/259 |
| 4,058,412 A | 11/1977 | Knapp et al. | |
| 4,084,723 A | 4/1978 | Parker | |
| 4,090,635 A | 5/1978 | Nelson et al. | |
| 4,108,336 A | 8/1978 | Anderson, Jr. | |
| 4,112,948 A | 9/1978 | Kurtz et al. | 128/276 |
| 4,135,515 A | 1/1979 | Muriot | 128/276 |
| 4,157,718 A | 6/1979 | Baehr | 128/276 |
| 4,195,633 A | 4/1980 | Nehring et al. | 128/276 |
| 4,195,672 A | 4/1980 | Freeman | |
| 4,228,798 A | 10/1980 | Deaton | 128/276 |
| 4,238,892 A | 12/1980 | Geiss | 34/85 |
| 4,245,637 A | 1/1981 | Nichols | 128/276 |
| 4,258,824 A | 3/1981 | Kurtz et al. | 181/233 |
| 4,275,732 A | 6/1981 | Gereg | 128/276 |
| 4,306,557 A | 12/1981 | North | 128/276 |
| 4,341,568 A | 7/1982 | Christensen | 134/21 |
| 4,345,342 A | 8/1982 | Saito | 4/301 |
| 4,356,084 A | 10/1982 | Hatton et al. | |
| 4,363,340 A | 12/1982 | Naftulin | 141/51 |
| 4,379,455 A * | 4/1983 | Deaton | 604/320 |
| 4,384,580 A | 5/1983 | Leviton | 604/119 |
| 4,388,922 A | 6/1983 | Telang | 604/319 |
| 4,429,803 A | 2/1984 | Butterfield | 215/366 |
| 4,430,084 A | 2/1984 | Deaton | |
| 4,430,085 A | 2/1984 | Ahrens | 604/321 |
| 4,455,140 A | 6/1984 | Joslin | 604/317 |
| 4,484,920 A | 11/1984 | Kaufman et al. | 604/416 |
| 4,516,973 A * | 5/1985 | Telang | 604/319 |
| 4,519,427 A | 5/1985 | Ono et al. | 141/65 |
| 4,540,413 A | 9/1985 | Russo | 604/320 |
| 4,559,664 A | 12/1985 | Bohme et al. | 15/302 |
| 4,586,549 A | 5/1986 | White | 141/67 |
| 4,629,159 A | 12/1986 | Wellenstam | 251/149.6 |
| 4,631,050 A | 12/1986 | Reed et al. | 604/4 |
| 4,666,063 A | 5/1987 | Holoubek et al. | 222/107 |
| 4,673,006 A | 6/1987 | Speck | 141/1 |
| 4,676,281 A | 6/1987 | Nord | 141/1 |
| 4,676,287 A | 6/1987 | Fitzwater | 141/285 |
| 4,685,480 A | 8/1987 | Eck | 134/182 |
| 4,698,060 A | 10/1987 | D'Antonio et al. | 604/320 |
| 4,704,106 A | 11/1987 | Shave et al. | 604/319 |
| 4,715,855 A | 12/1987 | D'Antonio et al. | 604/320 |
| 4,735,610 A | 4/1988 | Akkas et al. | 604/119 |
| 4,740,202 A | 4/1988 | Stacey et al. | 604/119 |
| 4,749,010 A | 6/1988 | Petell | 141/59 |
| 4,762,241 A | 8/1988 | Lang | |
| 4,770,787 A | 9/1988 | Heath et al. | 210/646 |
| 4,781,707 A | 11/1988 | Boehringer et al. | 604/317 |
| 4,785,963 A | 11/1988 | Magley | 220/266 |
| 4,795,428 A | 1/1989 | Hwang | 604/73 |
| 4,795,448 A | 1/1989 | Stacey et al. | 604/319 |
| 4,808,159 A | 2/1989 | Wilson et al. | 604/4 |
| 4,809,860 A | 3/1989 | Allen | 220/20.5 |
| 4,813,563 A | 3/1989 | Ogden et al. | |
| 4,820,351 A | 4/1989 | Hambleton et al. | 134/21 |
| 4,857,063 A | 8/1989 | Glenn | 604/317 |
| 4,863,446 A | 9/1989 | Parker | 604/317 |
| 4,867,738 A | 9/1989 | Mintz | 604/4 |
| 4,870,975 A | 10/1989 | Cronk et al. | 128/749 |
| 4,889,531 A | 12/1989 | D'Antonio et al. | 604/319 |
| 4,902,284 A | 2/1990 | D'Antonio et al. | 604/320 |
| 4,905,325 A | 3/1990 | Colditz | |
| 4,913,179 A | 4/1990 | Engel et al. | 134/113 |
| 4,913,197 A | 4/1990 | Friedrich | 441/3 |
| 4,926,915 A | 5/1990 | Deussen et al. | 141/290 |
| 4,955,874 A | 9/1990 | Farrar et al. | 604/319 |
| 4,957,491 A | 9/1990 | Parker | |
| 4,961,440 A | 10/1990 | Wright | |
| 4,967,814 A | 11/1990 | Day, Jr. | 141/286 |
| 4,969,491 A | 11/1990 | Kiplinger | 141/1 |
| 4,972,976 A | 11/1990 | Romero | |
| 5,011,470 A | 4/1991 | Kurtz et al. | 604/4 |
| 5,024,613 A | 6/1991 | Vasconcellos | 604/4 |
| 5,026,358 A | 6/1991 | Everett, Jr. et al. | 604/320 |
| 5,027,872 A | 7/1991 | Taylor et al. | 141/347 |
| 5,033,492 A | 7/1991 | Mertens et al. | 134/166 R |
| 5,045,077 A | 9/1991 | Blake, III | 604/321 |
| 5,049,273 A * | 9/1991 | Knox | 210/406 |
| 5,053,026 A | 10/1991 | Andersen et al. | 604/319 |
| 5,064,101 A | 11/1991 | Richter et al. | |
| 5,067,950 A | 11/1991 | Broadnax, Jr. | 604/317 |
| 5,071,035 A | 12/1991 | Kiplinger | 222/83.5 |
| 5,078,677 A | 1/1992 | Gentelia et al. | 604/4 |
| 5,119,830 A | 6/1992 | Davis | 128/771 |
| 5,121,778 A | 6/1992 | Baker et al. | 141/319 |
| 5,154,712 A | 10/1992 | Herweck et al. | 604/321 |
| 5,185,007 A * | 2/1993 | Middaugh et al. | 604/320 |
| 5,186,195 A | 2/1993 | Wall | |
| 5,192,439 A | 3/1993 | Roth et al. | 210/485 |
| 5,195,994 A | 3/1993 | Dieringer | 604/283 |
| 5,217,038 A | 6/1993 | Pinder | 137/216 |
| 5,222,530 A | 6/1993 | Baker et al. | |
| 5,242,434 A | 9/1993 | Terry | 604/317 |
| 5,273,083 A | 12/1993 | Burrows | 141/18 |
| 5,300,050 A | 4/1994 | Everett, Jr. et al. | 604/320 |
| 5,338,194 A * | 8/1994 | Strohmaier | 433/82 |
| 5,349,995 A | 9/1994 | Perez | 141/98 |
| 5,351,859 A | 10/1994 | Jansen | 222/82 |
| 5,380,314 A | 1/1995 | Herweck et al. | 604/403 |
| 5,437,836 A | 8/1995 | Yamada | 422/1 |
| 5,460,193 A | 10/1995 | Levallois et al. | |
| 5,470,324 A | 11/1995 | Cook et al. | 604/319 |
| 5,546,979 A | 8/1996 | Clark, II et al. | 137/318 |
| 5,599,331 A | 2/1997 | Hemstreet et al. | 604/317 |
| 5,620,428 A | 4/1997 | Hand | 604/317 |
| 5,624,417 A | 4/1997 | Cook et al. | 604/319 |
| 5,637,103 A | 6/1997 | Kerwin et al. | 604/317 |
| 5,683,371 A | 11/1997 | Hand | 604/317 |
| 5,688,255 A | 11/1997 | Hand | 604/317 |
| 5,725,516 A | 3/1998 | Cook et al. | 604/319 |
| 5,741,237 A | 4/1998 | Walker | 604/317 |
| 5,776,260 A | 7/1998 | Dunn et al. | 134/18 |
| 5,807,359 A | 9/1998 | Bemis et al. | 604/322 |
| 5,837,103 A | 11/1998 | Trokhan et al. | |
| 5,871,476 A | 2/1999 | Hand | 604/317 |
| 5,901,717 A | 5/1999 | Dunn et al. | 134/56 R |
| 5,931,822 A | 8/1999 | Bemis et al. | 604/322 |

* cited by examiner

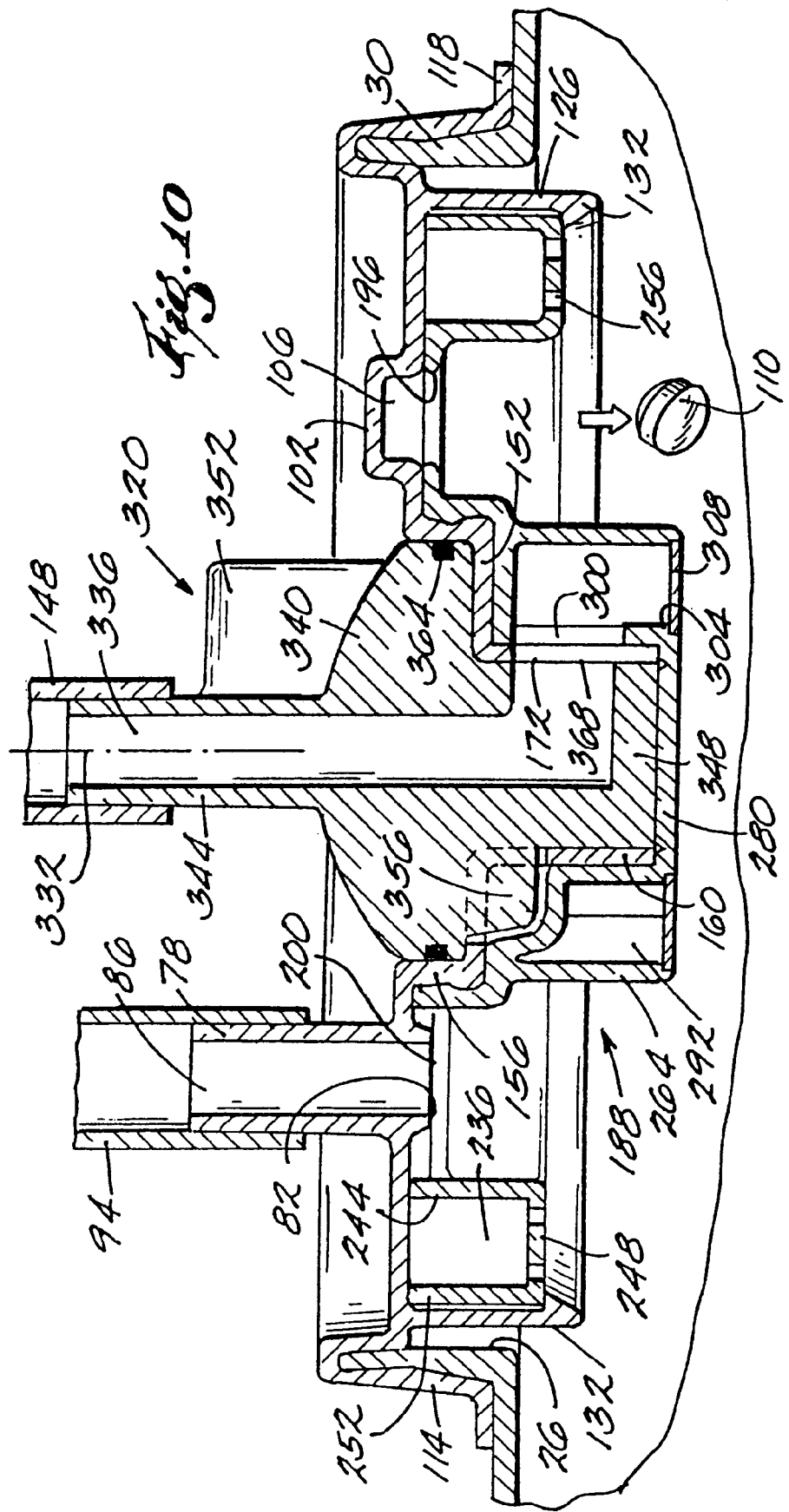

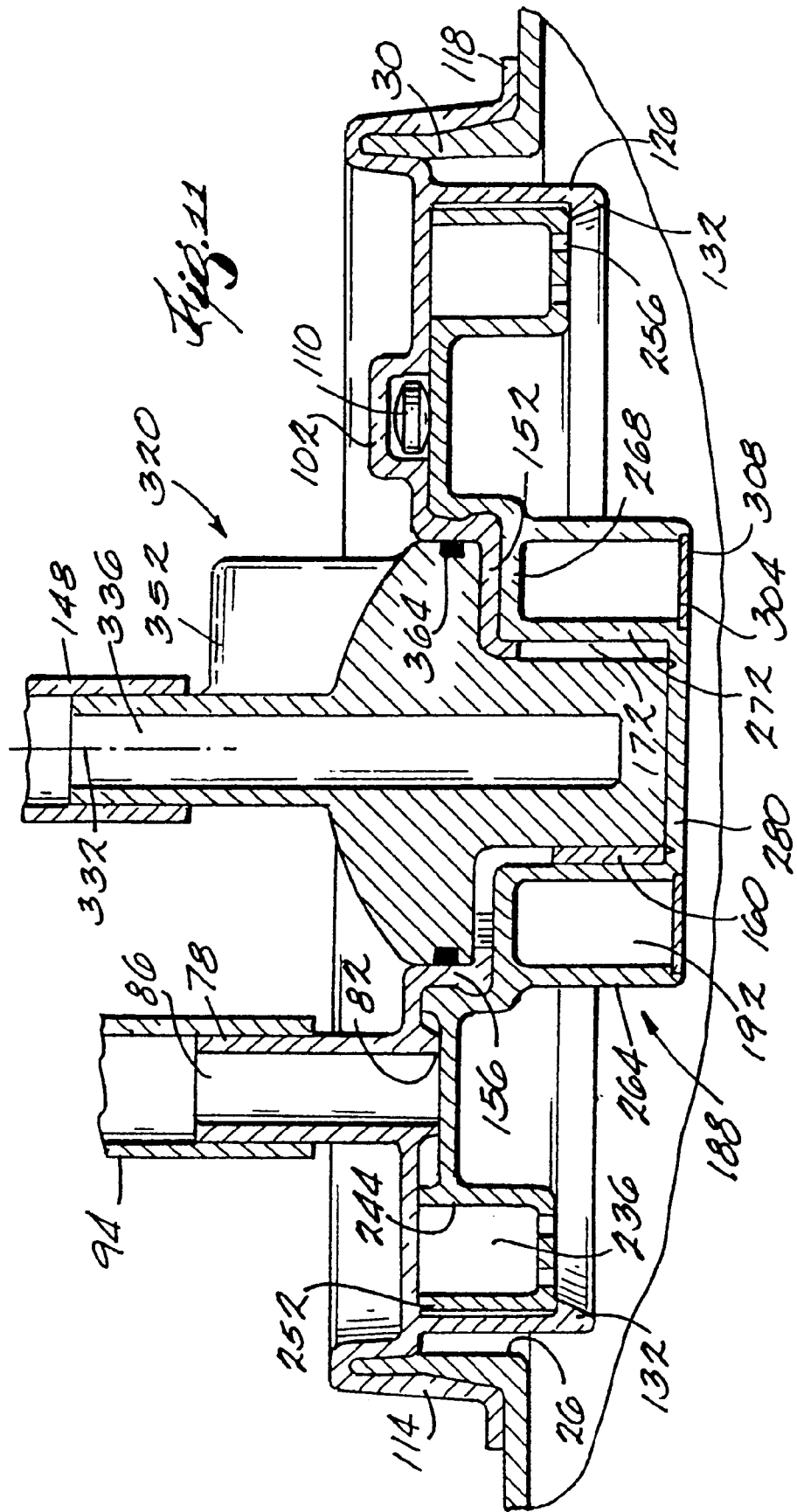

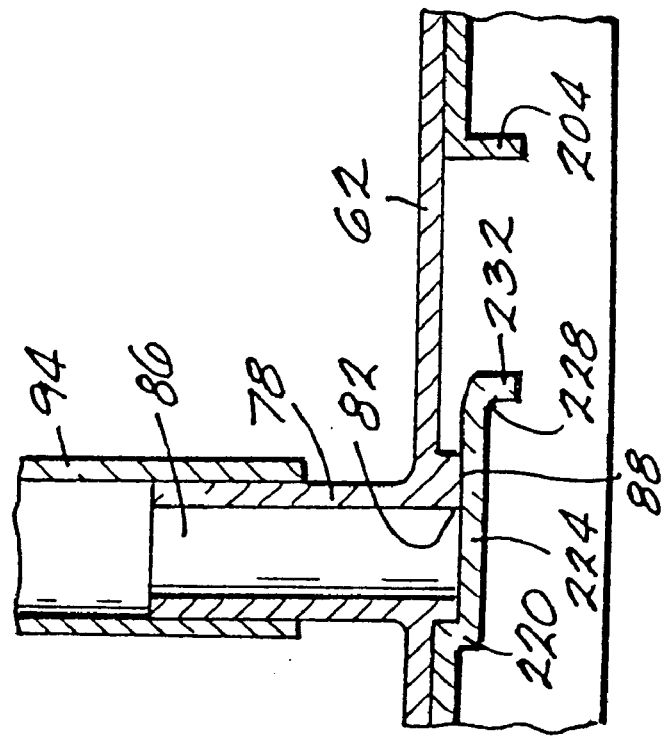
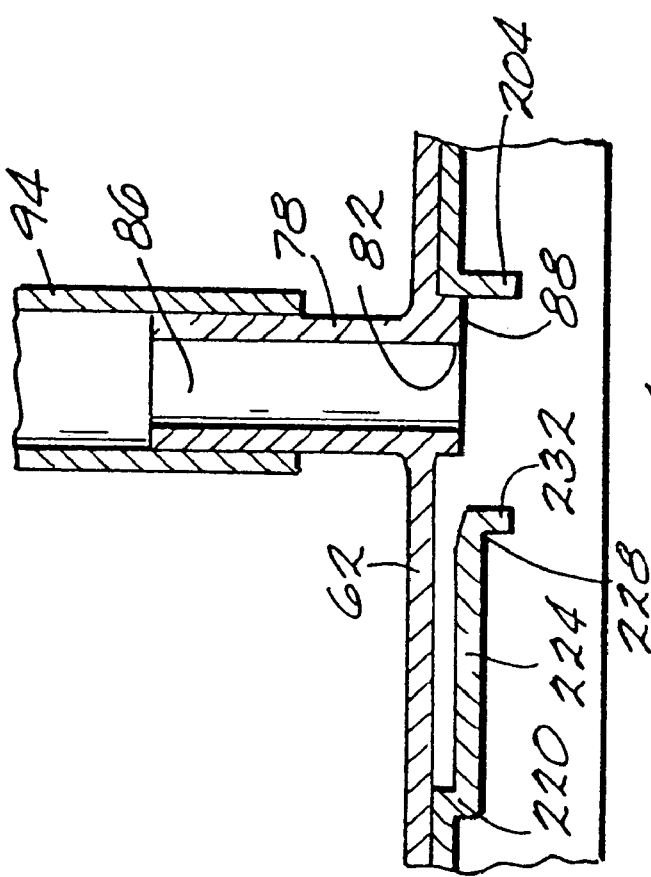

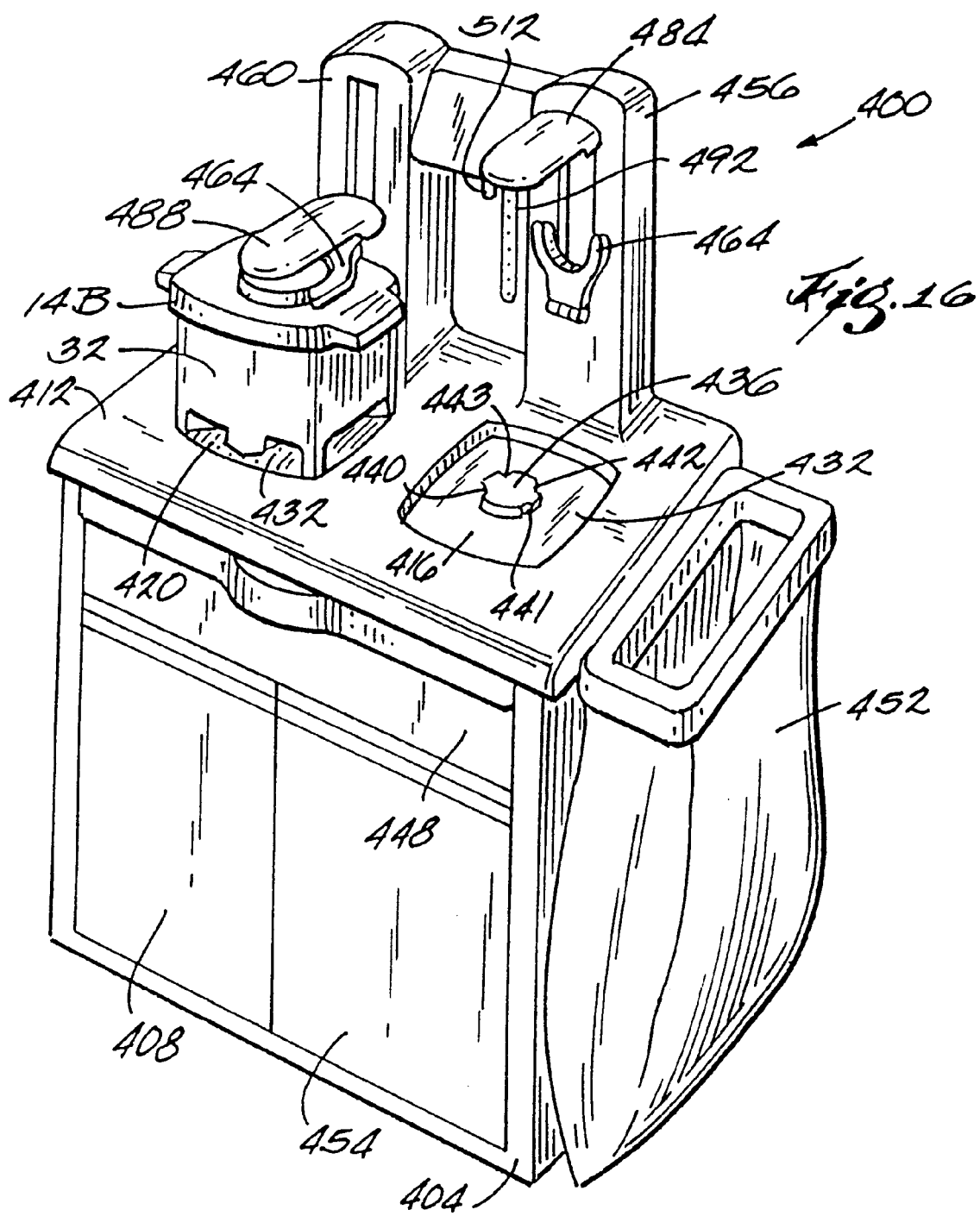

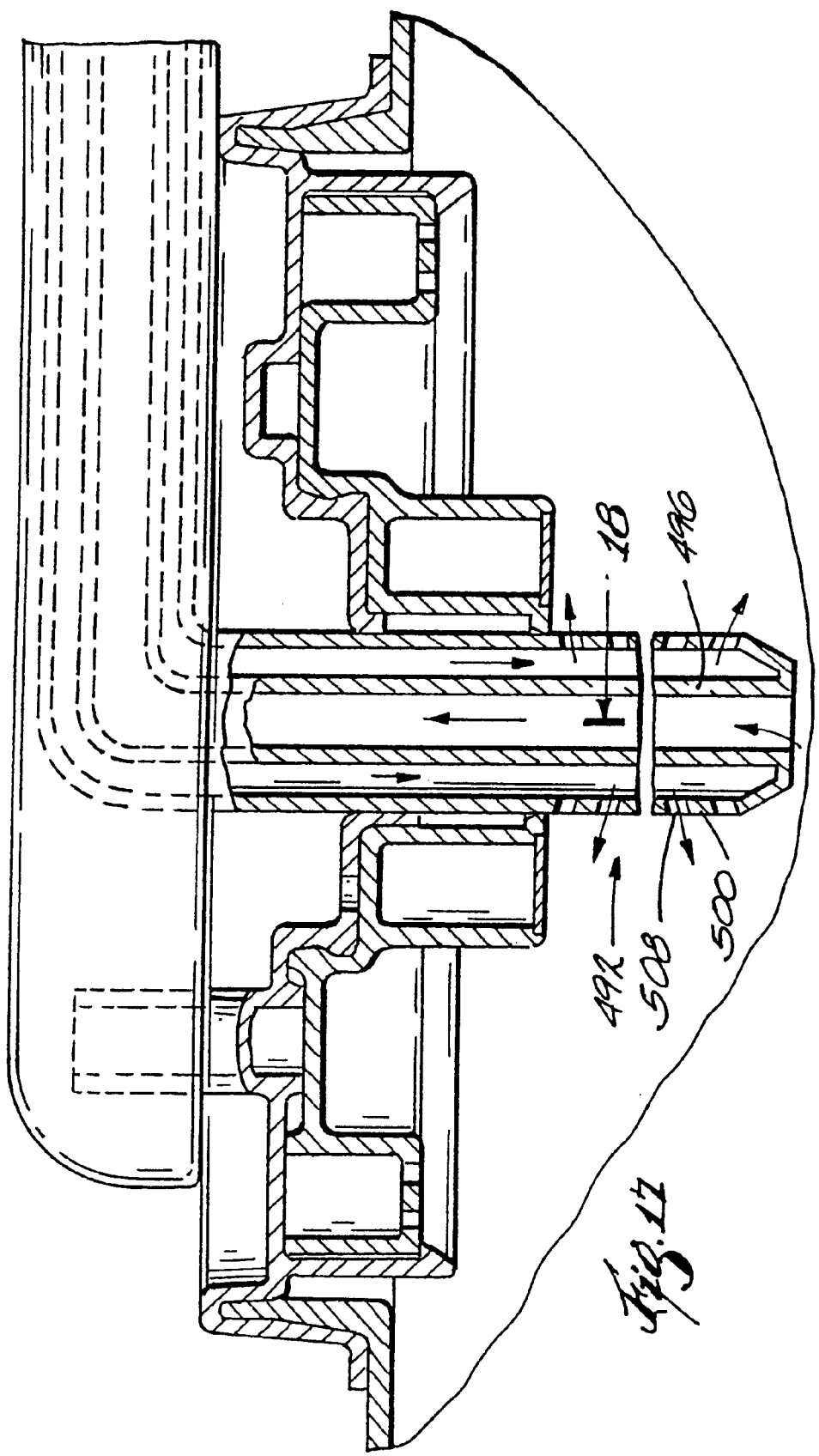

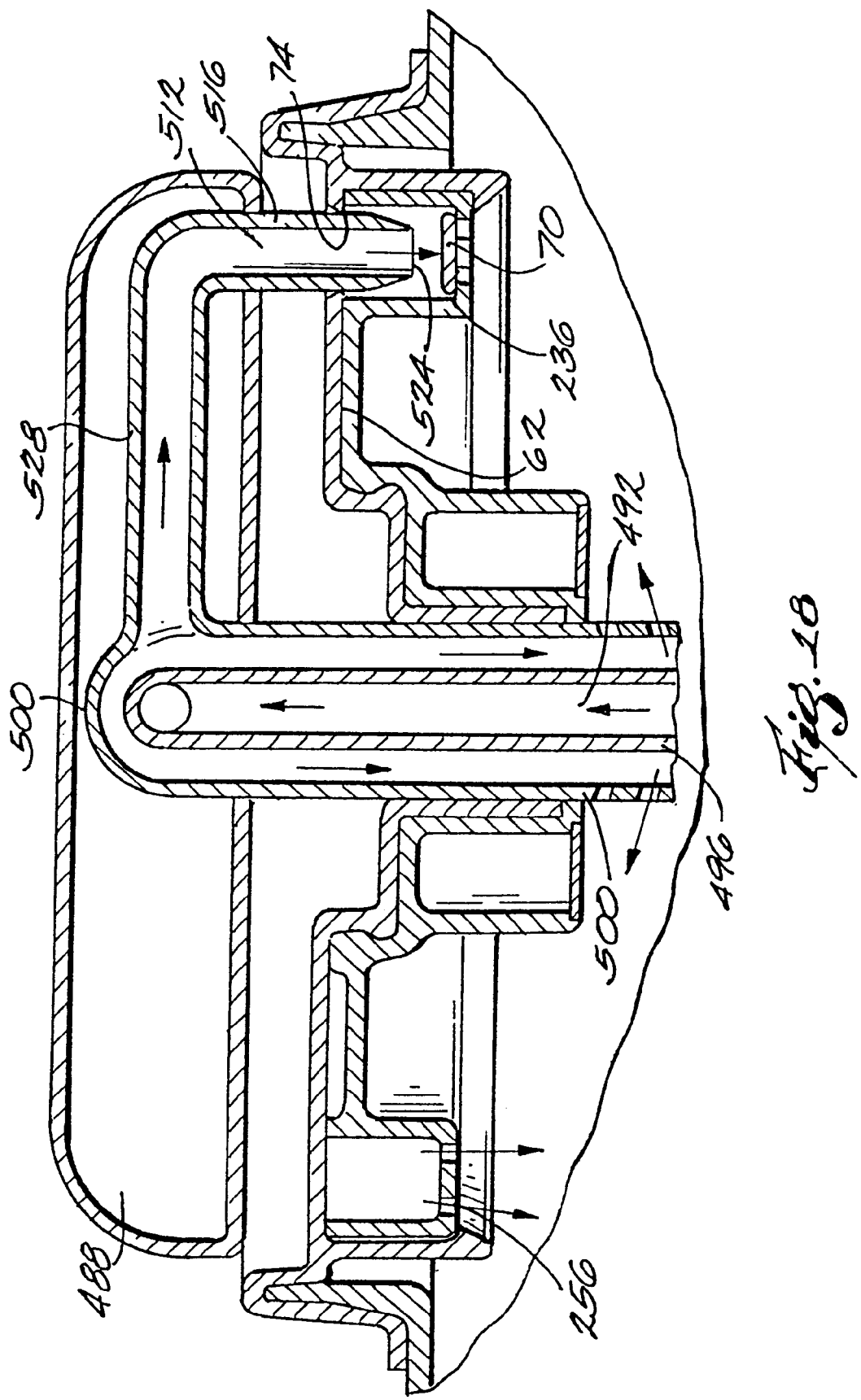

MEDICAL SUCTION SYSTEM

This patent application is a continuation of application Ser. No. 09/152,632, filed Sep. 14, 1998, now U.S. Pat. No. 5,931,822 which is a continuation of application Ser. No. 08/073,108, filed Jun. 8, 1993, now U.S. Pat. No. 5,807,359.

FIELD OF THE INVENTION

The invention relates to a medical suction system used in the collection of fluids such as from a patient during a surgical procedure.

BACKGROUND OF THE INVENTION

Medical suction systems are used in hospital environments and particularly during various surgical procedures to drain bodily fluid from a patient. In general, medical suction systems employ a collection or suction canister and a vacuum source which enables bodily fluid to be drained from the patient. Each canister generally includes a receptacle for holding the bodily fluid, a lid with a suction port and a patient port, a suction conduit connecting the suction port to a hospital vacuum system, and a patient conduit for conveying the bodily fluid from the patient into the receptacle through the patient port. When the vacuum is applied to the suction conduit, a negative pressure gradient is created in the interior of the receptacle so that the bodily fluid is drawn from the patient and into the suction canister via the patient conduit. In order to prevent the bodily fluid from entering and contaminating the hospital vacuum system, a shutoff valve is normally used to close or block the suction port when the fluid within the canister rises to a predetermined level.

Conventional suction canisters are often disposable, which leads to increased hospital costs for the purchase of new canisters and increased hospital costs for the disposal of the canisters and their bodily fluid contents after use. Suction canisters can also be reusable. However, such reusable canisters must be cleaned by hospital employees, and the bodily fluid collected in suction canisters is considered hazardous and infectious waste. In recent years, it has become important in hospital environments to eliminate the handling and thus reduce employee exposure to bodily fluids. Currently, hospitals dispose of such bodily fluid in three ways. The fluid is either poured from the suction canister down the hospital sink, the fluid is incinerated in a hospital-owned and operated pathological incinerator, or expensive contracts are negotiated with a licensed hauler for the disposal of the fluid at an approved hazardous waste incinerator. In every case, hospital employees have to handle the bodily fluid. Spattering of the bodily fluid can result in hospital employees contacting the hazardous fluid and thus increasing the possibility of contacting HIV, Hepatitis B or other blood borne diseases.

SUMMARY OF THE INVENTION

The invention provides a cover for an opening in a suction canister receptacle used in draining bodily fluid from a patient. The cover includes a main body for substantially covering the opening in the receptacle. The main body defines a suction port and a suction passageway for connection to a vacuum source, a patient port for communication with the patient, and a cleaning port. The cover also includes means for dispensing a cleaning agent into the canister in response to the introduction of cleaning fluid into the cleaning port, for opening the patient port in response to opening of the suction port, for closing the patient port in response to closing of the suction port, and treatment means for introducing a chemical treatment into the interior of the receptacle in response to opening of the patient port.

The invention also provides a cleaning station which includes means for automatically draining and cleaning the suction canister. The cleaning station includes upper and lower housings with the lower housing supporting the suction canister. The upper housing includes first and second cleaning probes which are inserted into the suction canister in response to downward movement of the upper housing. The first probe is inserted into the suction passageway and the second probe is inserted into the cleaning port. The probes in cooperation with the cover introduce a cleaning fluid and a cleaning agent into the suction canister and drain the suction canister of bodily fluid and cleaning fluid.

The invention also provides means for automatically providing a visible indication that the canister has been cleaned. The means includes a seal that is broken and a portion of the cover that is punched out, both by insertion of the probes into the cover when the suction canister is drained and cleaned.

It is one object of the invention to provide a medical suction system that includes reusable suction canister receptacles.

It is another object of the invention to provide a medical suction system that includes disposable covers for the reusable suction canister receptacles.

It is another object of the invention to provide a medical suction system in which the disposable covers include a moveable cartridge.

It is another object of the invention to provide a suction canister in which the patient port is opened when the suction port is opened and is closed when the suction port is closed.

It is another object of the invention to provide a medical suction system that filters the air being drawn into a vacuum source to prevent contamination of the vacuum source.

It is another object of the invention to provide a medical suction system that introduces a chemical treatment into a suction canister when the suction canister is connected to a vacuum source.

It is another object of the invention to provide a medical suction system that includes a cleaning station which drains and disposes of the bodily fluid held in a suction canister and then cleans the canister without hospital personnel contacting the bodily fluid held therein.

It is another object of the invention to provide a medical suction system that utilizes a cleaning instrument to drain and clean a suction canister.

It is another object of the invention to provide a medical suction system that provides a visible indication that a suction canister receptacle has been drained and cleaned.

It is another object of the invention to provide a medical suction system that dispenses a cleaning agent into a suction canister in response to the introduction of a cleaning fluid into the canister.

Other features and advantages of the invention will become apparent to those of ordinary skill in the art upon review of the following detailed description, claims, and drawings.

BRIEF DESCRIPTION OF THE DRAWINGS

FIG. 10 is a sectional view of the suction canister cover taken along line 10—10 in FIG. 3 with the cartridge in the open position;

FIG. 11 is a view similar to FIG. 10 showing the cartridge in the closed position;

FIG. 12 is a partial sectional view taken along line 12—12 of FIG. 3 with the cartridge in the open position;

FIG. 13 is a view similar to FIG. 12 showing the cartridge in the closed position;

FIG. 14 is a perspective view of the key;

FIG. 15 is a bottom plan view of the key;

FIG. 16 is a perspective view of the cleaning station of the medical suction system;

FIG. 17 is a partial sectional view of a suction canister supported by the cleaning station with a first probe of the cleaning station inserted in the canister;

FIG. 18 is a sectional view taken along line 18—18 in FIG. 17;

Figure 1:
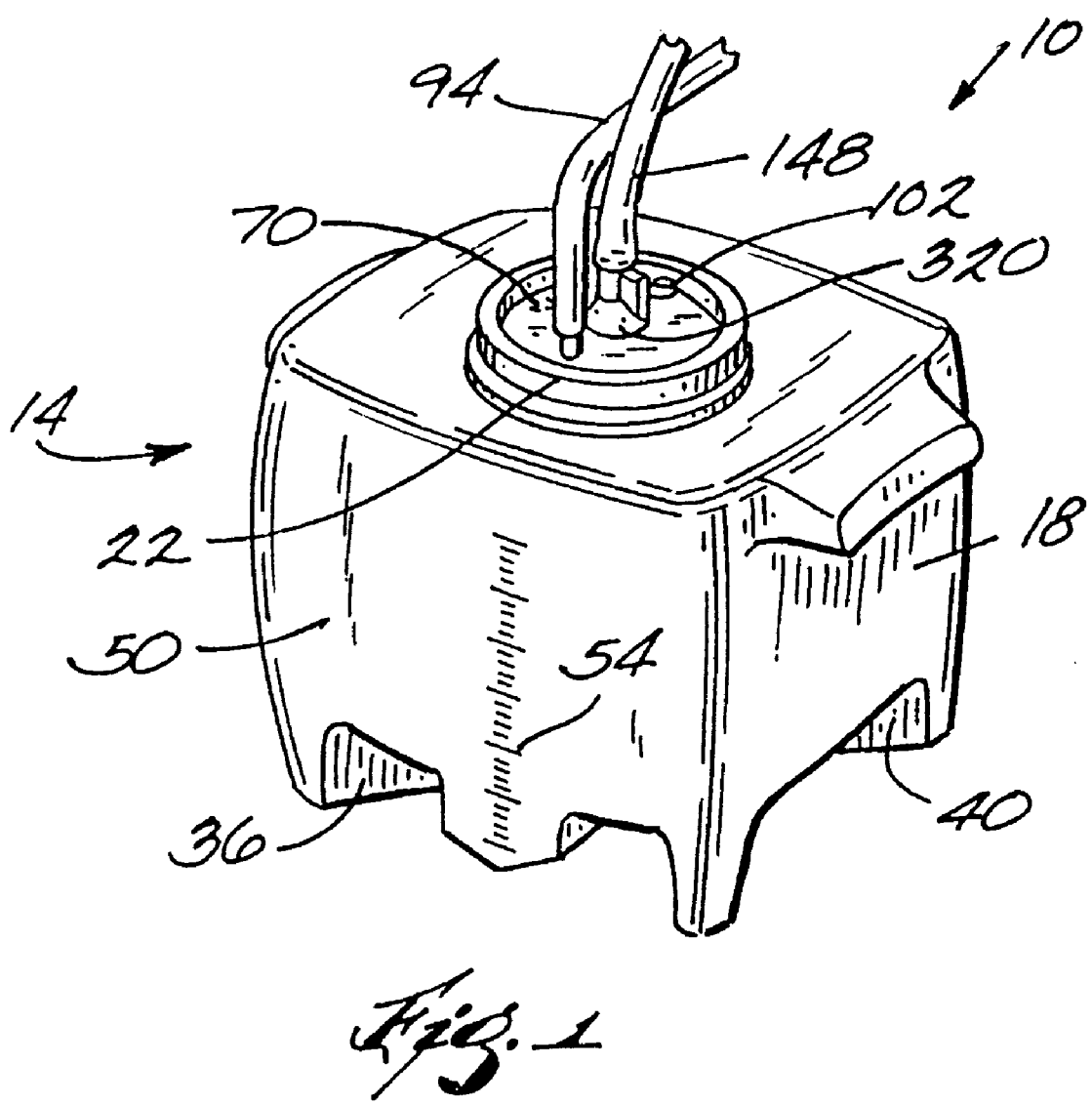
FIG. 1 is a perspective view of a suction canister embodying the invention.

Before one embodiment of the invention is explained in detail, it is to be understood that the invention is not limited in its application to the details of construction and the arrangement of components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

DETAILED DESCRIPTION OF THE PREFERRED EMBODIMENT

Figure 2:
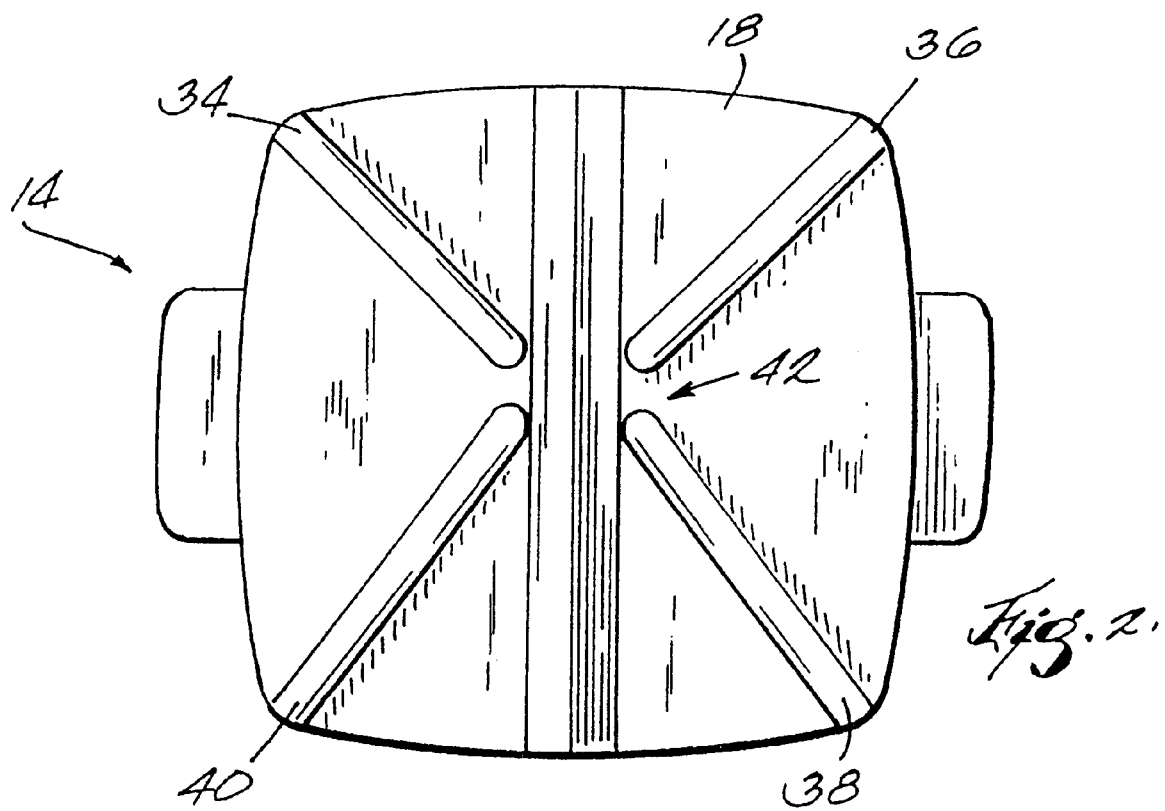
FIG. 2 is a bottom view of the suction canister.

Referring now to the drawings in which like reference numerals refer to like parts throughout the views, there is shown a medical suction system 10 embodying the invention. The system 10 comprises (see FIG. 1) a suction canister 14 which includes a receptacle 18 and a disposable cover 22. The receptacle 18 is closed except for an opening or receptacle port 26 at the top, the receptacle port 26 being defined by an annular receptacle port wall 30 (FIGS. 10 and 11). In the preferred embodiment, the receptacle 18 is manufactured of clear unbreakable plastic with a total volume capacity of 4000 cc of fluid. The receptacle can be manufactured as one integral piece or as two pieces, a top portion and a bottom portion, that are fixed together by sonic welding or other suitable means. As best shown in FIGS. 1 and 2, the receptacle has on its lower surface 32 four generally radially extending projections 34, 36, 38, 40 that do not hold fluid. The inner ends of the four projections 34, 36, 38, 40 define a recess 42 in the lower surface 32. The receptacle 18 also defines a critical measure area located at the bottom-most portion of the receptacle interior. The critical measure area is of V-shaped cross-section at its lower-most end and extends across the receptacle 18. On the outer surface 50 of the receptacle 18 are gradation lines 54 that correspond to various fluid volume levels. As the suction canister receptacle 18 begins to fill with fluid, the critical measure area 46 enables the reading of very small fluid quantities using the gradation lines 54.

Figure 5:
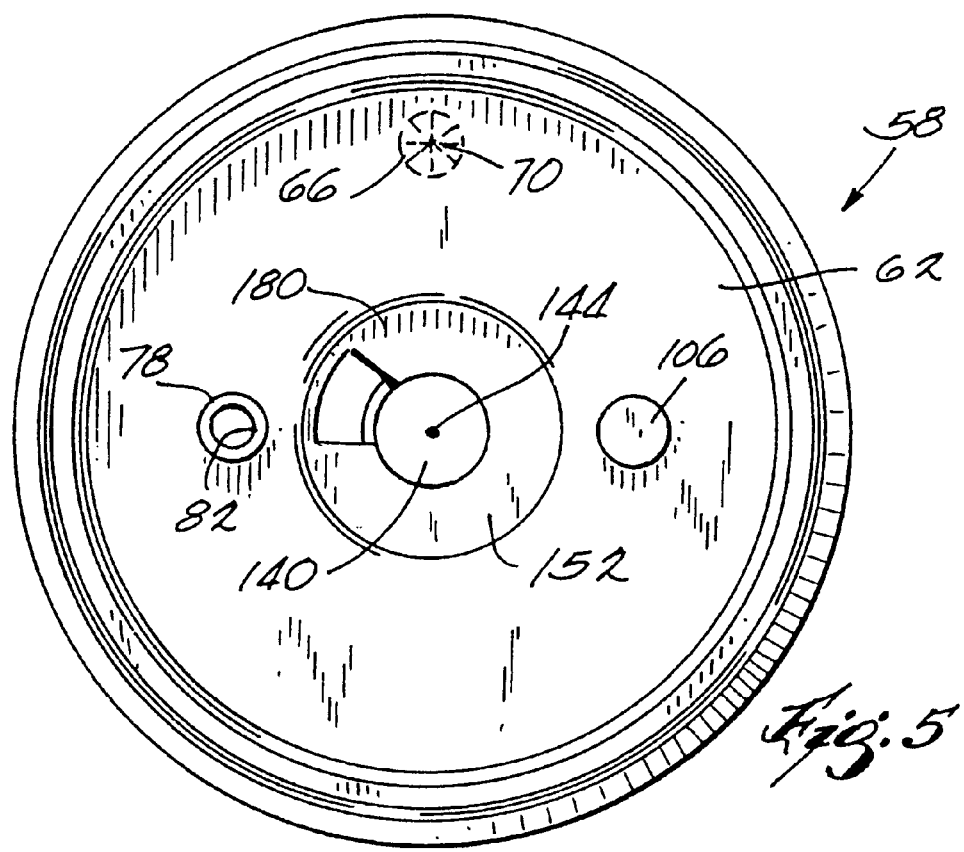
FIG. 5 is a top plan view of the main body.
Figure 6:
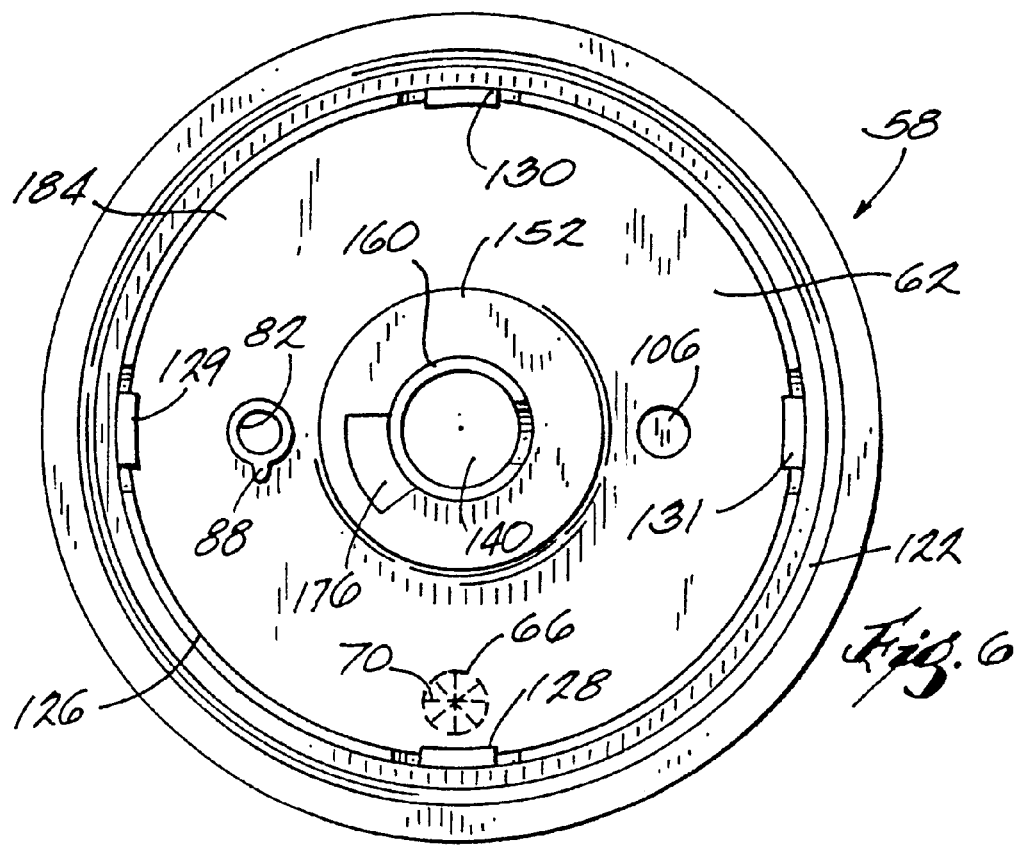
FIG. 6 is a bottom plan view of the main body.

The cover 22 closes the receptacle port 26, thus sealing the interior of the suction canister 14. Referring to FIGS. 3 through 6, the cover 22 includes a main body 58 having a top wall 62. A weakened portion 66 of the top wall 62 defines a cleaning port cover 70 that can be punched out to define a cleaning port 74 (FIG. 18) in the top wall 62. An annular patient port wall 78 extends upwardly and downwardly from the top wall 62 and defines a patient port 82 and a fluid passageway 86 (FIGS. 10 and 11) extending upwardly from the patient port 82. Further, as shown in FIGS. 4 and 6, a stop member 88 projects outwardly from the portion of the patient port wall 78 that extends downwardly from the top wall 62.

To enable communication between the patient and the patient port 82, one end of a patient conduit 94 is affixed to the cover 22 by forcing the patient conduit 94 over the patient port wall 78 as depicted in FIGS. 10 and 11. The fluid passageway 86 thus communicates with the patient conduit 94. The other end of the patient conduit 94 communicates with the patient (not shown).

Figure 3:
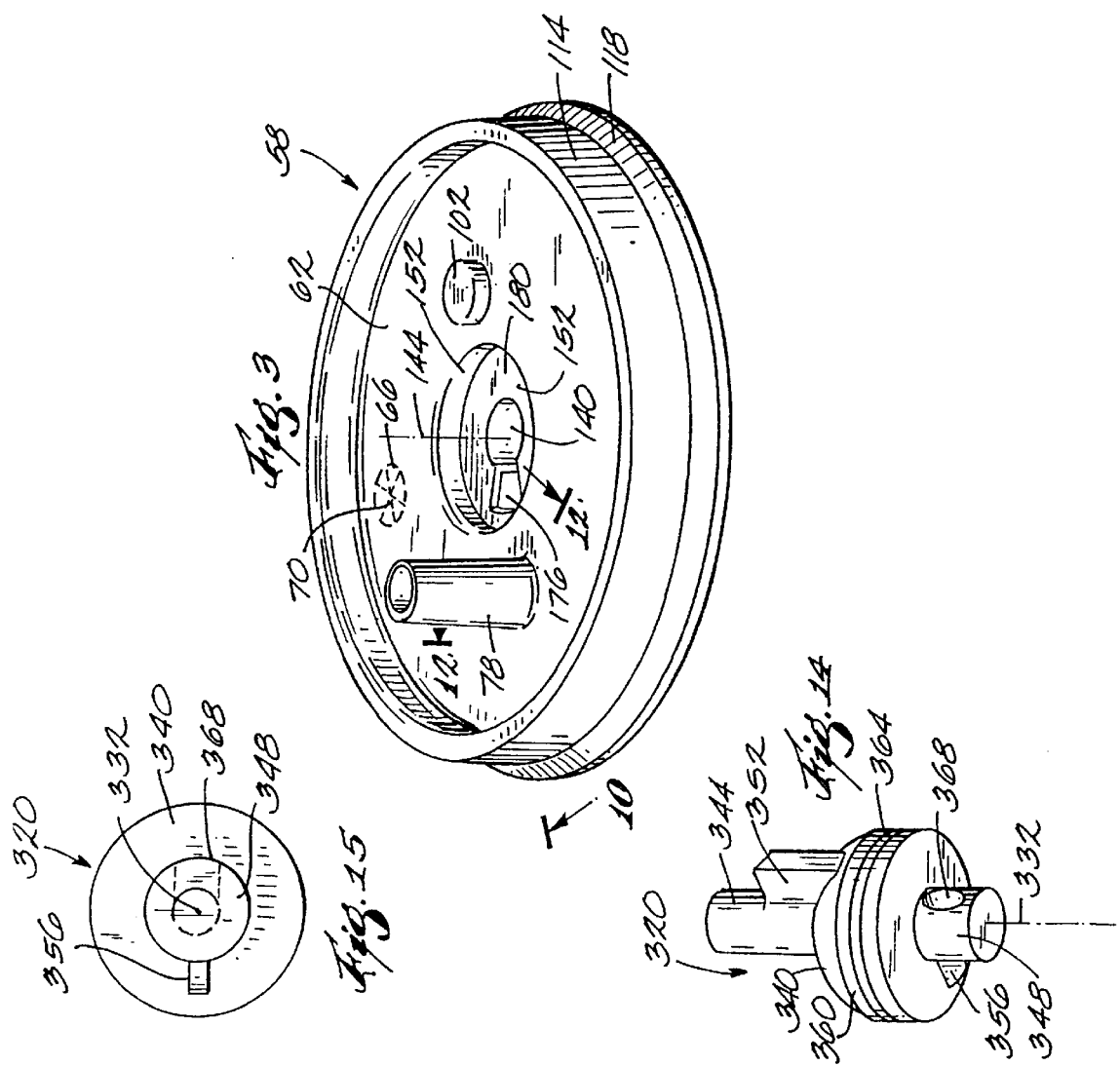
FIG. 3 is a top perspective view of the main body of the suction canister cover.
Figure 4:
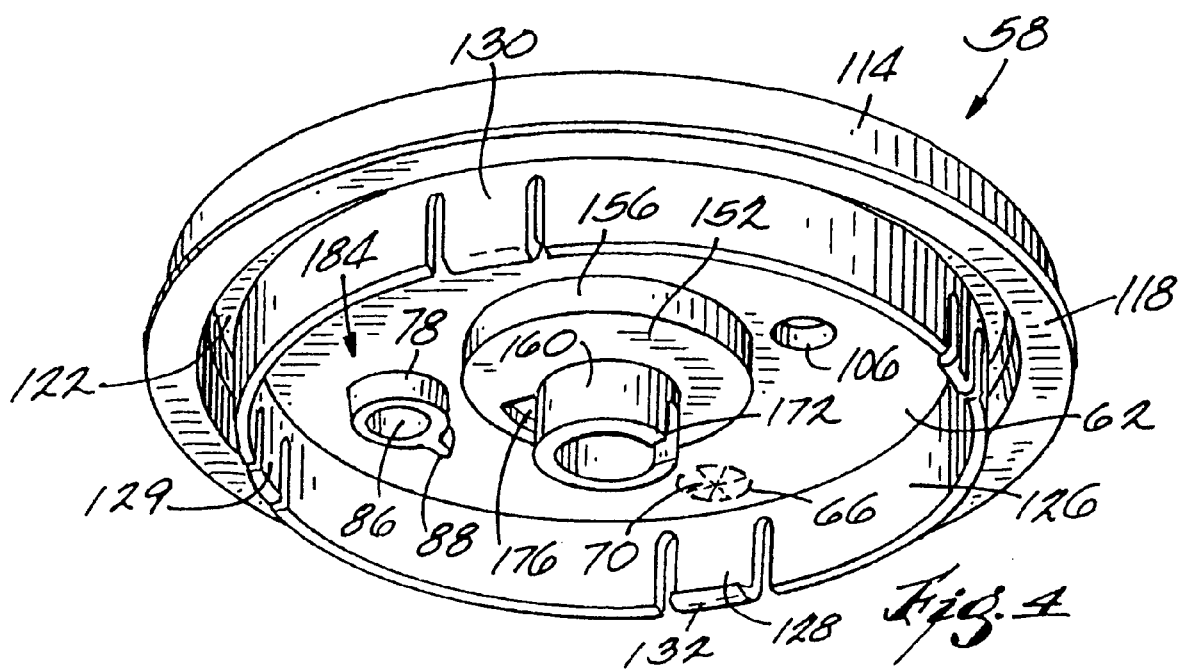
FIG. 4 is a bottom perspective view of the main body.

As best shown in FIGS. 3 and 4, a boss 102 extends upwardly from the top wall 62 and defines a downwardly opening treatment chamber 106. The treatment chamber 106 holds a chemical treatment 110 (FIG. 11). In the preferred embodiment, the chemical treatment is an anti-foaming and anti-coagulating agent such as citric acid in the form of a tablet. However, it should be appreciated that the chemical treatment 110 can be any type of chemical used to treat the bodily fluid while the fluid is held in the receptacle 18.

Referring to FIGS. 3 through 6, the main body 58 also includes an annular sidewall 114 extending from the periphery of the top wall 62. The sidewall 114 includes an outwardly extending annular flange 118. The sidewall 114 defines an annular recess 122 as best seen in FIGS. 4 and 6. To secure the cover 22 to the receptacle 18, the receptacle port wall 30 is positioned in the recess 122 such that the flange 118 rests on the receptacle 18 as shown on FIGS. 10 and 11. Preferably, a friction fit secures the receptacle port wall 30 in the recess 122. Alternatively, the cover 22 could thread onto the receptacle port wall 30 or could be connected thereto by other means.

As best seen in FIGS. 4 and 6, an annular socket wall 126 depends from the underside of the top wall 62. The socket wall 126 defines four spaced locking tabs 128, 129, 130, 131. The lower end of each locking tab has thereon a radially inwardly extending lip 132.

Referring to FIGS. 3 and 4, the main body 58 also defines a suction passageway 140 having a longitudinal axis 144. The suction passageway 140 is connectable with a hospital vacuum system via a suction conduit 148 (FIGS. 1, 10 and 11), as will be explained later. The suction passageway 140 is centrally located within the main body 58 and has an upper end surrounded by a horizontal annular wall 152. The horizontal wall 152 is connected to the top wall 62 by an interior annular wall 156 that depends from the top wall 62. The horizontal wall 152 extends radially inwardly from the lower end of the interior wall 56. Further, an annular suction port wall 160 depends from the inner radial edge of the horizontal wall 152 and further defines the suction passageway 140. The lower end of the suction port wall 2160 as therein a notch defining a suction port 172 communicating with the lower end of the suction passageway 140. As best seen in FIGS. 3 and 5, the horizontal wall 152 and the suction port wall 160 cooperate to define an arcuate notch 176, and the interior wall 156, the horizontal wall 152 and the suction port wall 160 cooperate to define a key holder socket 180 in the top of the main body 58. Further, as best seen in FIGS. 4 and 6, the underside of the top wall 62, the underside of the horizontal wall 152 and the socket wall 126 define a cartridge socket 184 in the underside of the main body 58.

Figure 7:
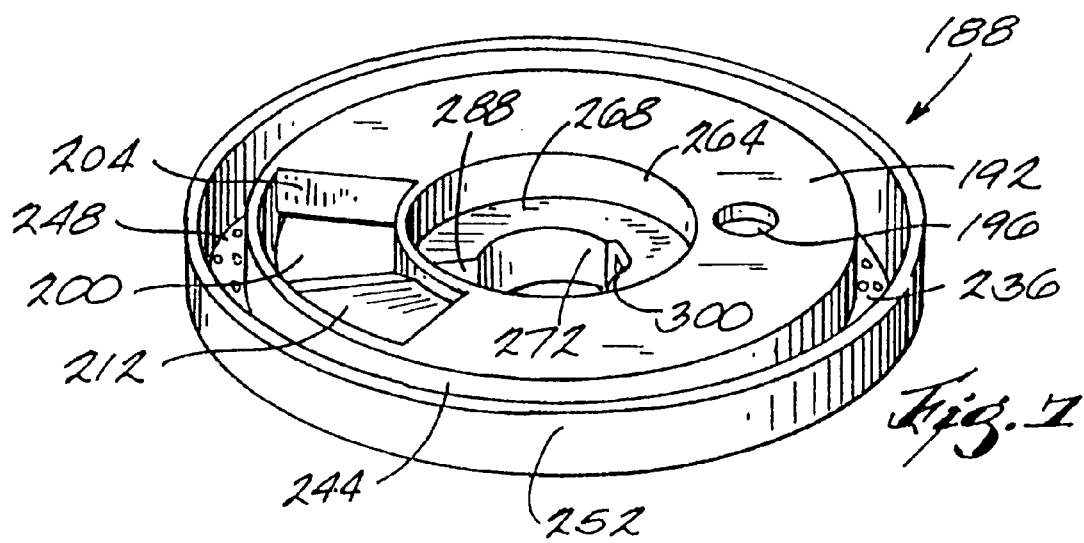
FIG. 7 is a top perspective view of the cartridge of the suction canister cover.
Figure 8:
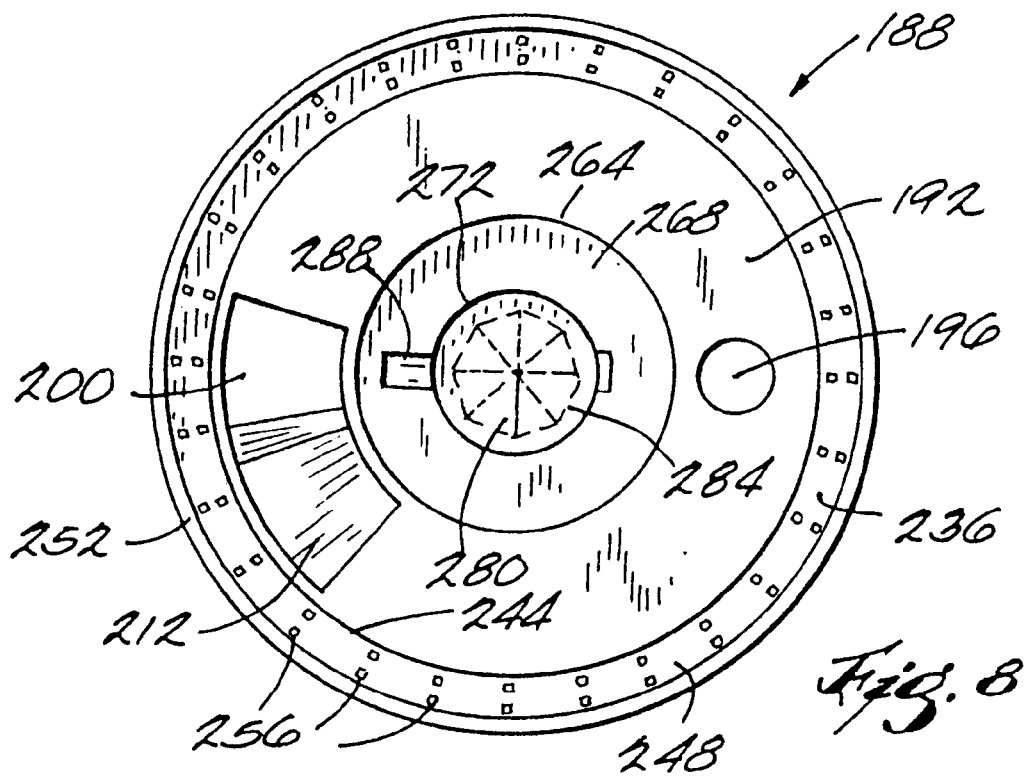
FIG. 8 is a top plan view of the cartridge.
Figure 9:
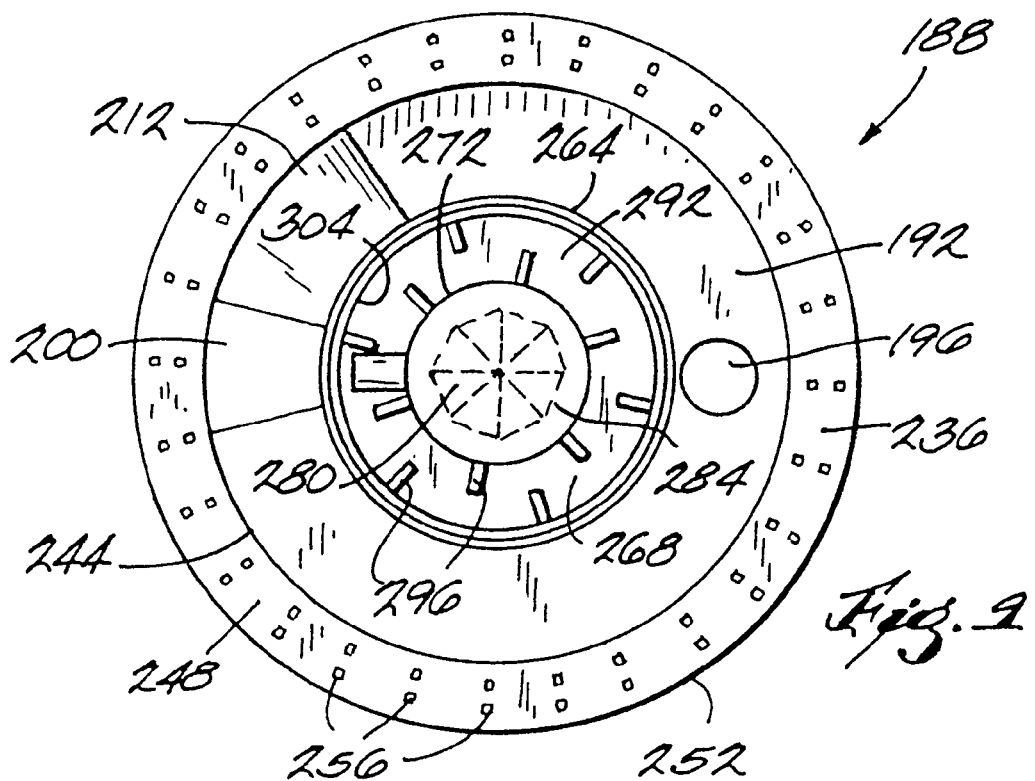
FIG. 9 is a bottom plan view of the cartridge.

Referring now to FIGS. 7 through 9, the cover 22 also includes means for dispensing a cleaning agent into the receptacle in response to the introduction of a cleaning fluid into the cleaning port 74, means for opening the patient port 82 in response to opening of the suction port 172 and for closing the patient port in response to closing of the suction port 172, means for introducing a chemical treatment into the interior of the receptacle 18 in response to the opening of the patient port 82, and means for filtering air drawn through the suction port 140 when the suction port is connected to the vacuum source. All of the foregoing means include a cartridge 188 supported by the main body 58 for pivotal movement relative thereto about the axis 144 of the suction passageway 140 and between an open position (FIGS. 10 and 12) and a closed position (FIGS. 11 and 13). More specifically, the cartridge 188 is located in the cartridge socket 184. The lip 132 of each locking tab 128, 129, 130, 131 extends beneath the lower end of the cartridge 188 to retain the cartridge in the cartridge socket 184 (FIGS. 10 and 11).

As best seen in FIGS. 7 through 9, the cartridge 188 includes an annular top wall 192 having therein an aperture 196 for communication with the interior of the suction canister 14 and for selective communication with the treatment chamber 106. When the aperture 196 is aligned with the treatment chamber 106, the chemical treatment 110 drops into the receptacle 18 (FIG. 10). The aperture 196 is aligned with the treatment chamber 106 when the cartridge 188 is in the open position, as shown in FIG. 10, and is not aligned with the treatment chamber 106 when the cartridge 188 is in the closed position, as shown in FIG. 11. The top wall 192 also has therein (see FIGS. 7–9, 12 and 13) an arcuate inlet 200 which communicates with the interior of the receptacle 18 and which selectively communicates with the patient port 82. A first end wall 204 depends from the top wall 192 and defines one end of the inlet 200. The top wall 192 includes a recessed ramp portion 212 that defines the other end 216 of the inlet 200. As shown in FIGS. 12 and 13, the ramp portion 212 consists of a vertical segment 220, a horizontal segment 224, and a ramp segment 228 that terminates in a second end wall 232. As shown in FIG. 13, the horizontal segment 224 tightly engages the lower end of the wall 78 and closes the patient port 82 when the cartridge 188 is in the closed position. The tight engagement between the horizontal segment 224 and the wall 78 substantially seals the patient port 82. The patient port 82 is aligned with the inlet 200 when the cartridge 188 is in the open position, as shown in FIG. 12. The bottom of the patient port wall 78 moves up the ramp segment 228 to the horizontal segment 224 when the cartridge 188 moves from the open position to the closed position.

As depicted in FIGS. 7–11, the cartridge 188 also defines an annular cleaning chamber 236 which communicates with the cleaning port 74 and contains a cleaning agent. The cleaning agent can be any suitable chemical or combination of chemicals, such as a detergent, that aids in cleaning the interior of the suction canister 14. The cleaning chamber 236 is defined by a first annular inner wall 244, a bottom wall 248 and an outer wall 252. The inner wall 244 depends from the periphery of the top wall 192, the bottom wall 248 extends radially outwardly from the lower portion of the inner wall 244, and the outer wall 252 extends upwardly from the bottom wall 248. The top of the cleaning chamber 236 is closed by the top wall 62 of the main body 58. The cartridge 188 also defines a cleaning chamber outlet in the form of a plurality of spaced outlets 256 in the bottom wall 248 that allow the cleaning agent to flow into the interior of the receptacle 18 in response to the introduction of a cleaning fluid into the cleaning port 74. The cleaning of the suction canister will be discussed in greater detail in a later section.

Continuing to refer to FIGS. 7–11, the cartridge 188 has a second annular inner wall 264 depending from the inner periphery of the top wall 192. The second inner wall 264 is concentric with and radially inward of the first inner wall 244. The inlet 200 of the cartridge 188 is thus defined more specifically by the first and second end walls 204 and 232, respectively, and by portions of the first and second inner walls 244 and 264, respectively. Extending radially inwardly and horizontally from the second inner wall 264 is a horizontal annular wall 268, and depending from the inner edge of the wall 268 is a third annular inner wall 272. The wall 272 is concentric with the walls 244, 264 and is the most inward of these three walls. The lower end of the wall 272 is closed by a removable member or seal 280 having thereon score lines 284. The wall 272 also has therein a recess 288 (see FIGS. 8 and 10).

Referring to FIGS. 9–11, the underside of the wall 268 and the walls 264, 272 define a filter passageway or filter chamber 292. Within the filter passageway 292 are ribs 296 (FIG. 9) extending radially inwardly and outwardly from the walls 264, 272. The wall 272 has therein a filter passageway outlet 300. As shown in FIG. 10, the filter passageway outlet 300 communicates with the suction port 172 and thus with the suction passageway 140 when the cartridge 188 is in the open position (FIG. 10). The filter passageway 292 is closed by the suction port wall 160 when the cartridge 188 is in the closed position (FIG. 11). The annular area between the lower-most portions of the walls 264, 272 defines a filter passageway inlet 304. A suitable filter 308 (FIGS. 10 and 11) is located in the inlet 304 and is supported by the ribs 296. The filter 308 prevents air flowing from the interior of the receptacle 18 to the vacuum source from contaminating the vacuum source. The filter 308 can, if desired, be hydrophobic.

Referring to FIGS. 10 and 11, the cartridge 188 is positioned in the cartridge socket 184 such that the wall 272 surrounds the suction port wall 160 of the main body 58, the wall 268 is adjacent the horizontal wall 152 of the main body 58, the top wall 192 is adjacent the top wall 62 of the main body 58, the seal 280 closes the lower end of the suction passageway 140, and the recess 288 is visible within the arcuate notch 176 of the main body 58.

In the open position as shown in FIG. 10, the cartridge 188 is positioned in the cartridge socket 184 such that the aperture 196 is in alignment with the treatment chamber 106, the filter passageway outlet 300 is in alignment with the suction port 172, and the cartridge inlet 200 is in alignment with the patient port 82 and the fluid passageway 86. In the closed position as shown in FIG. 11, the cartridge 188 is positioned in the cartridge socket 184 such that the aperture 196 is out of alignment with the treatment chamber 106, the filter passageway outlet 300 is out of alignment with the suction port 172, and the cartridge inlet 200 is out of alignment with the patient port 82 and the fluid passageway 86.

The movement of the cartridge 188 relative to the main body 58 between the open and closed positions is limited in the counterclockwise direction (as seen from above) by the stop member 88 contacting the first end wall 204 of the cartridge 188 (FIG. 12). The movement of the cartridge 188 relative to the main body 58 is limited in the clockwise direction (as seen from above) by the lower portion of the patient port wall 78 contacting the vertical segment 220 of the ramp portion 212 of the cartridge 188 (FIG. 13). The cartridge 188 thus has a limited range of motion relative to the main body 58. In the preferred embodiment, that range of motion is 45 degrees between the two positions.

Referring to FIGS. 10, 11, 14 and 15, to rotate the cartridge 188 relative to the main body 58 between the open and closed positions, the medical suction system 10 utilizes a key 320 communicating with one end of the suction conduit 148. The other end of the suction conduit 148 communicates with the hospital vacuum system (not shown). The key 320 has a longitudinal axis 332 and defines an air passageway 336 (FIGS. 10 and 11). The key 320 includes a main portion 340, an upper annular portion 344, a lower cylindrical portion 348, a turning tab 352 extending upwardly from the main portion 340 and outwardly from the upper portion 344, and a projection 356 extending downwardly from the main portion 340 and outwardly from the cylindrical portion 348. The main portion 340 has a cylindrical outer surface 360 having therein a groove housing an annular sealing or O-ring 364. The upper portion 344 extends upwardly from the main portion 340 and is centered on the longitudinal axis 332 of the key 320. The air passageway 336 extends from the upper end of the upper portion 344, through the main portion 340 and into the cylindrical portion 348. The lower portion 348 of the key 320 depends from the main portion 340 and is centered on the longitudinal axis 332 of the key. The lower portion 348 has therein a key inlet 368 which communicates with the air passageway 336. To connect the suction conduit 148 to the key 320 and to the air passageway 336, the end of the conduit 148 is forced over the upper portion 344 (FIGS. 10 and 11). The turning tab 352 facilitates rotation of the key 320 about its longitudinal axis 332.

The rotation of the cartridge 188 relative to the cover 22 is accomplished as follows with reference to FIGS. 10 and 11. Assuming the cartridge 188 is in the closed position (FIG. 11), the key 320 is inserted into the key holder socket 180 of the cover 22 such that the projection 356 on the key 320 extends through the arcuate notch 176 in the main body 58 and into the recess 288 in the cartridge 188. In this position, the lower portion 348 of the key 320 fills the suction passageway 140, the main portion 340 rests against the wall 156, and the O-ring 364 sealingly engages the wall 156 to prevent fluid leaks. To rotate the cartridge 188 to the open position (FIG. 10), the turning tab 352 of the key 320 is gripped and the key 320 is turned 45 degrees (counterclockwise as viewed from above) until movement is inhibited. The engagement of the projection 356 of the key 320 with the recess 288 in the cartridge 188 causes movement of the cartridge 188 relative to the main body 58 when the key 320 is rotated about its longitudinal axis 332. To return the cartridge 188 to the closed position, the key 320 is rotated clockwise 45 degrees until the movement is inhibited.

The operation of the medical suction system 10 in its fluid collection capacity is as follows. A clean or unused cover 22 is attached to a clean suction canister receptacle 18 with the cartridge 188 in the closed position relative to the main body 58. One end of the patient conduit 94 is connected to the patient port wall 78 of the cover 22 to allow communication between the patient port 82 and the patient conduit 94. The other end of the patient conduit 94 communicates with the patient. The key 320 is connected to one end of the suction conduit 148 to enable communication between the air passageway 336 of the key 320 and the suction conduit 148. The other end of the suction conduit 148 is connected to the hospital vacuum system. The key 320 is then placed into the key holder socket 180 and the cartridge 188 is rotated to the open position. When the cartridge 188 is moved to the open position, the treatment chamber 106 and the aperture 196 move into alignment so that the chemical treatment 110 that was housed in the treatment chamber 106 falls into the interior of the receptacle 18 as shown in FIG. 10. In the open position, air from the interior of the receptacle 18 travels through the filter passageway inlet 304, through the filter 308, through the filter passageway 292 and its outlet 300, through the suction port 172, through the key inlet 368, along the air passageway 336 of the key 320, and then through the suction conduit 148 to the hospital vacuum system. This creates a vacuum in the receptacle 18. As a result of the vacuum in the receptacle 18, fluid from the patient travels through the patient conduit 94, through the fluid passageway 86 and the patient port 82 of the main body 58, and then through the inlet 200 in the cartridge 188 to the interior of the receptacle 18.

When fluid collection is no longer desired or the suction canister 14 is filled with bodily fluid, the key 320 is rotated to return the cartridge 188 to the closed position. This closes both the filter passageway outlet 300 and the fluid passageway 86, thereby stopping fluid flow through the patient conduit 94. The key 320 is then removed from the key holder socket 180. The suction canister 14 is then ready to be drained and cleaned as will now be described.

Figure 19:
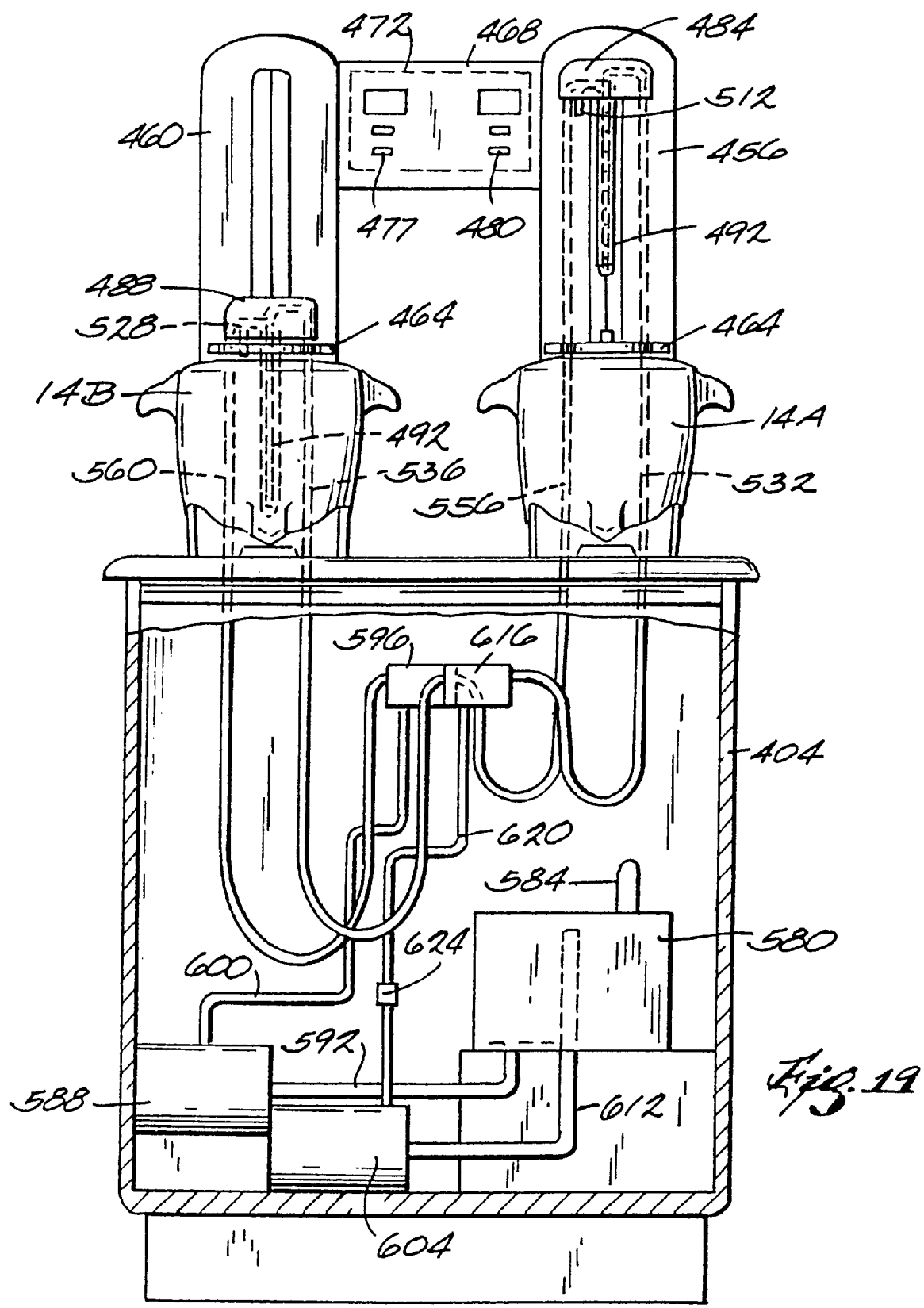
FIG. 19 is a front elevational view, partially broken away, of the cleaning station.

Turning to FIG. 16, the medical suction system 10 also comprises a cleaning station 400 which includes means for automatically draining and cleaning the suction canister 14 without a hospital employee contacting the hazardous and infectious bodily fluid contained therein. The cleaning station includes a lower housing 404 comprising a cabinet 408 with an upper surface 412. The upper surface 412 has thereon first and second cradles 416 and 420, respectively, for supporting right and left suction canisters 14A and 14B. Each cradle 416, 420 is defined by (see FIG. 16) a recess 432 which is substantially the same size as the bottom-most portion of a suction canister 14. A stub 436 extends upwardly from the center of the recess 432 and has therein four V-shaped notches 440, 441, 442, 443. To orient a suction canister 14 relative to the cleaning station 400, the suction canister 14 is placed into the recess 432 such that the inner ends of the four projections 34, 36, 38 and 40 are respectively received in the four notches 440, 441, 442, 443 and the stub 436 is received in the receptacle recess 42. The notches 440, 441, 442, 443 and the receptacle projections 34, 35, 36, 37 are arranged so that the suction canister 14 must be oriented with the front face 32 forward in order to locate the bottom of the suction canister 14 in the recess 42. FIG. 19 depicts both suction canisters 14A, 14B oriented relative to the cleaning station 400. Thus, the cradles 416, 420 and the suction canisters 14A, 14B comprise interengaging means for orienting the suction canisters 14A, 14B relative to the cleaning station 400. The cabinet 408 further includes a drawer 448, and an attached waste container 452 (shown only in FIG. 16). Doors 454 afford access to the interior of the cabinet 408.

Continuing to refer to FIG. 16, the lower housing 404 also comprises spaced-apart, right and left support posts 456 and 460, respectively, extending upwardly from the upper surface 412 of the cabinet 408. Each post 456, 460 has thereon a holding bracket 464 which is pivotable from an upwardly projecting position as shown on the right post 456 to a horizontally projecting position as shown on the left post 460. A control panel 468 extends between the posts 456, 460. The control panel 468 includes a controller 472 such as a suitably programmed microprocessor. The panel 468 also includes operational buttons such as a START button 477, status indicators (preferably conventional LED displays) and a deadman switch 480, all of which are connected to the controller 472.

The cleaning station 400 further includes a right upper housing 484 moveable vertically relative to the right post 456 and a left upper housing 488 moveable vertically relative to the left post 460. The movement of each upper housing is caused by a hydraulic assembly 490 within the associated support post 456 or 460. Only the hydraulic assembly 490 in the left post 460 is shown (see FIG. 20). The upper housings 484, 488 extend forwardly from their respective posts 456, 460. Each upper housing 484, 488 has depending therefrom, adjacent the forward end thereof, a first cleaning probe 492. As shown in FIGS. 17 and 18, the probe 492 includes an inner conduit 496 and an outer conduit 500. The inner conduit 496 communicates with a vacuum source and has an opening 504 (FIG. 17) in its lower end. The outer conduit 500 surrounds the inner conduit 496, communicates with a source of cleaning fluid, and has therein a plurality of outlet openings 508 spaced along its length. The outlets 508 are slanted upwardly near the top of the outer conduit 500 and downwardly near the bottom.

Referring to FIGS. 16 and 18, each upper housing 484, 488 also has depending therefrom, at a point spaced laterally from the first probe 492, a second cleaning probe 512. The second probe 512 includes a single conduit 516 with a sharp or pointed lower end having therein an opening 524. The conduit 516 communicates with the outer conduit 500 of the first probe 492 via a horizontal conduit 528. The probes 492 and 512 move vertically with the upper housings 484, 488.

Figure 20:
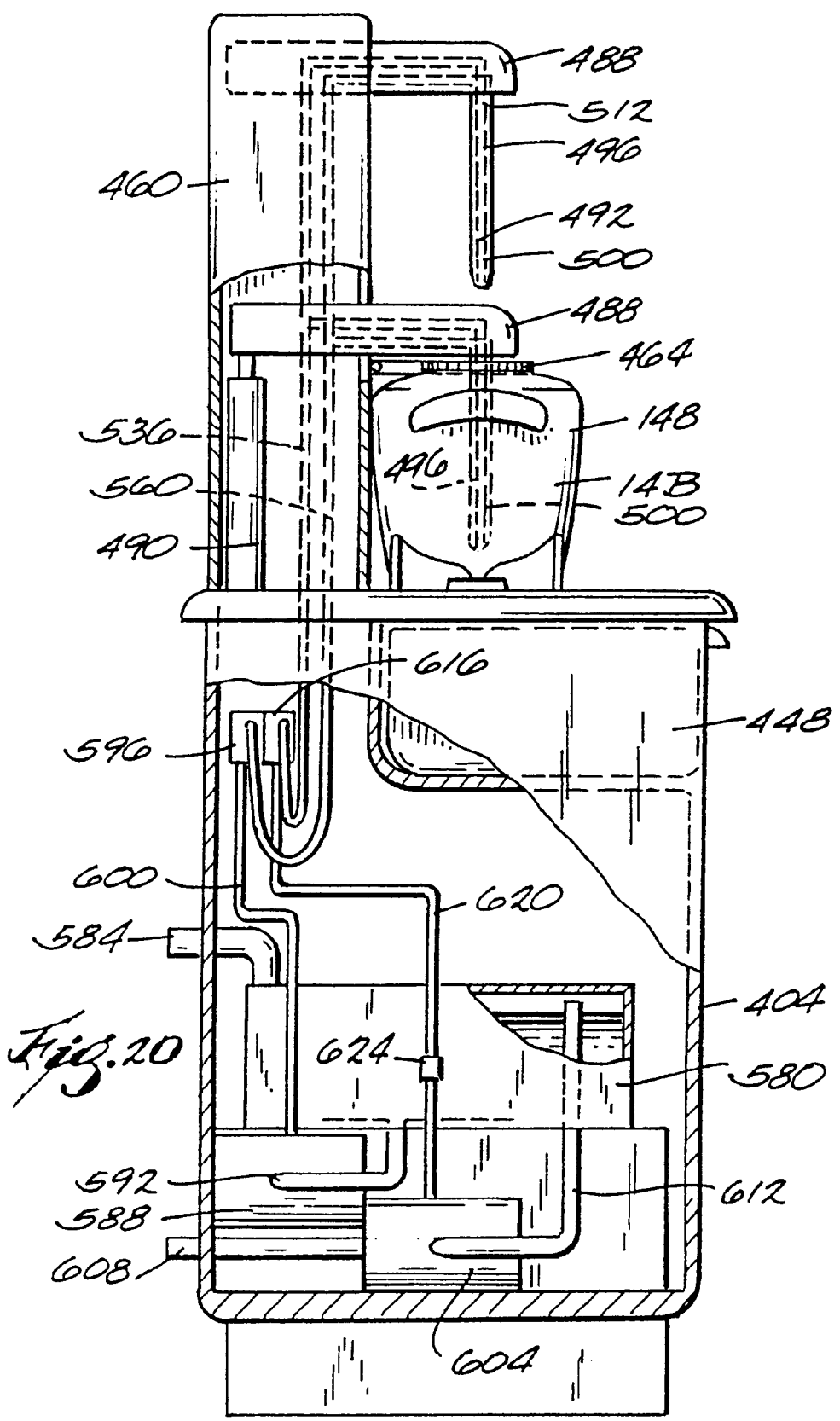
FIG. 20 is a left side elevational view, partially broken away, of the cleaning station.

As shown in FIGS. 19 and 20, the cleaning station 400 also includes, inside the lower housing 404, right and left suction conduits 532 and 536, respectively. The upper end of the conduit 532 communicates with the inner conduit 496 of the right upper housing 484, and the upper end of the conduit 536 communicates with the inner conduit 496 of the left upper housing 488. The lower ends of the conduits 532, 536 are selectively connectable to a vacuum source as described below. The cleaning station 400 also includes right and left water supply conduits 556 and 560, respectively. The upper end of the conduit 556 communicates with the outer conduit 500 of the right upper housing 484, and the upper end of the conduit 560 communicates with the outer conduit 500 of the left upper housing 488. The lower ends of the conduits 556, 560 are selectively connectable to a source of cleaning fluid as will be described below. In the preferred embodiment, the cleaning fluid utilized is water.

Referring again to FIGS. 19 and 20, the cleaning station 400 also includes, in the lower housing 404, a water supply reservoir 580 communicating with the hospital water supply via a first water supply line 584. The lower housing 404 also includes a water supply pump 588 connected to the water reservoir 580 by a second water supply line 592. The water supply pump 558 communicates with a water supply valve 596 via a third water supply line 600. The valve 596 communicates with the lower ends of the water supply conduits 556, 560. The water supply valve 596 diverts the water in the third supply line 600 to either the right water supply conduit 556 or the left water supply conduit 560 depending upon which of the two suction canisters 14A and 14B is being cleaned and drained.

To create the negative pressure gradient that enables draining of a suction canister, the cleaning station 400 includes a drain pump 604 shown in FIGS. 19 and 20. The drain pump 604 communicates with the hospital sewer system via a first drain line 608. The drain pump 604 also communicates with the water reservoir 580 via an overflow standpipe 612. If the volume of water in the water reservoir 580 exceeds a predetermined volume, the excess water will flow through the standpipe 612 and into the drain pump 604 to be discharged into the hospital sewer via the first drain line 608. As shown in FIG. 19, a vacuum valve 616 communicates with the drain pump 604 via a second drain line 620. The lower ends of the right and left suction conduits 532, 536 communicate with the vacuum valve 616. The vacuum valve 616 selectively connects either of the right and left suction conduits 532, 536 to the drain pump 604 via the second drain line 620. The second drain line 620 has therein an in-line sensor 624 that determines when fluid is no longer draining from a suction canister.

When a suction canister containing bodily fluid needs to be drained and cleaned, the suction canister 14 is oriented on one of the cradles 416, 420 of the cleaning station 400 as previously described. Although the cleaning station 400 has the capability of supporting two suction canisters 14A, 14B on the lower housing 404, only one suction canister 14 can be drained and cleaned at a time. After orienting the suction canister 14 on either cradle 416 or 420, the operator manually pivots the corresponding holding bracket 464 or 466 downwardly until the bracket contacts the suction canister 14. The operator then depresses the START button 477 to initiate a timed draining and cleaning cycle. If the holding bracket 464 or 466 has not been pivoted downwardly onto the suction canister 14, the controller 472 will not initiate the draining and cleaning cycle even if the START button 477 is depressed. By checking the positions of the holding brackets 464, 466 on the right and left posts 456, 460, the controller 472 determines which of the cradles 416, 420 has a suction canister thereon or if both cradles 416, 420 have a suction canister thereon. If both cradles 416, 420 have a suction canister thereon, the controller 472 will initiate the cleaning and draining of the left suction canister 14B first. If only one of the cradles 416 or 420 has a suction canister thereon with the holding bracket 464 or 466 pivoted downwardly, then the controller 472 will initiate the cleaning and draining cycle of that particular suction canister.

If the right suction canister 14A is to be drained and cleaned, the controller 472 sends a signal to the water supply valve 596 to provide communication between the right water supply conduit 556 and the third water supply line 600. The controller 472 also sends a signal to the vacuum valve 616 to provide communication between the right suction line 532 and the second drain line 620. Similarly, if the left suction canister 14B is to be cleaned and drained, the controller 472 sends a signal to the water supply valve 596 to provide communication between the left water supply conduit 560 and the third water supply line 600. The controller also sends a signal to the vacuum valve 616 to provide communication between the left suction conduit 536 and the second drain line 620. Hereafter, it will be assumed that the left suction canister 14B is being drained and cleaned as represented by FIG. 20.

Referring to FIGS. 18 and 20, the controller 472 sends a signal to the left hydraulic assembly 490 which causes the left upper housing 488 to move downwardly relative to the lower housing 404. As the left upper housing 488 is lowered, the first probe 492 also moves downwardly and is inserted into the left suction canister 14B through the suction passageway 140. As the probe 492 moves downwardly through the suction passageway 140, the probe 492 contacts the seal 280 on the cartridge 188. Further downward movement causes the probe 492 to break the seal 280 away from the cartridge. The seal 280 thus comprises a means for providing a visual indication that a suction canister has been cleaned and more particularly that a cleaning instrument or probe has been inserted into the suction passageway. The probe 492 acts as a means for altering the suction canister 14B in response to cleaning thereof.

After the seal 280 has been broken, the controller 472 continues to cause the downward movement of the left upper housing 488 and the probe 492 until the left upper housing 488 contacts the cover 22 of the suction canister 14B. The probe 492 now extends into the interior of the suction canister 14B.

Simultaneously as the first probe 492 is lowered, the second probe 512 is also lowered. Downward movement of the left upper housing 488 causes the probe 512 to contact the cleaning port cover 70. Further downward movement of the left upper housing 488 causes the probe 512 to punch out the cleaning port cover 70 from the top wall 62 of the cover 22, allowing the probe 512 to pass through the cleaning port 74. The cleaning port cover 70 thus also acts as a means for providing a visible indication that a cleaning fluid has been introduced into the cleaning port. The probe 512 acts as a means for altering the suction canister in response to cleaning thereof. When the downward movement of the left upper housing 488 ceases, the probe 512 is positioned in the cleaning chamber 236 of the cover 22 as depicted in FIG. 18.

After the first and second probes 492, 512 are in these positions, the cleaning and draining of the suction canister 14B begins. The controller 472 causes the drain pump 604 to create a negative pressure gradient inside the suction canister 14B via the second drain line 620 and the left suction conduit 536. The negative pressure gradient causes the bodily fluid held in the suction canister 14B to be taken up into the inner conduit 496, flow through the left suction conduit 536, flow through the second drain line 620, flow through the drain pump 604, and then flow into the hospital sewer system via the first drain line 608. After the suction canister 14B is substantially drained of bodily fluid as determined by the in-line sensor 624, the water pump 588 is activated by the controller 472. As a result, water from the water reservoir 580 flows through the second water supply line 592, through the water pump 588, through the third water supply line 600, through the left water supply conduit 560 and then into the outer conduit 500 of the probe 492 to be sprayed into the interior of the suction canister 14B via the outlets 508. The outlets 508 that are slanted upward near the top of the outer conduit 500 enable water to reach the bottom surface of the cover 22. The water also travels through the horizontal conduit 528 and into the conduit 516 of the second probe 512, then out of the open end 524 and into the cleaning chamber 236 where the water contacts the cleaning agent. The water and cleaning agent then pass through the cleaning chamber outlets 256 and into the interior of the suction canister 14B. As the water and cleaning agent accumulate in the interior of the suction canister 14B, the inner conduit 496 continues to drain the suction canister 14B. At any time during the draining and cleaning cycle, the deadman switch 480 can be activated to immediately shut down the cleaning station 400 in case of emergency.

The controller 472 controls the amount of time the water is being pumped into the suction canister 14B. When that time period is over, the controller 472 sends a signal to the water supply pump 588 to cease supplying the suction canister 14B with water. The controller 472 continues to have the drain pump 604 drain the remaining fluid from the suction canister 14B after the water pump 588 has ceased operating. In the preferred embodiment, the cleaning and draining cycle total time is approximately 120 seconds. When the draining and cleaning cycle is completed, the controller 472 sends a signal to the left hydraulic assembly 490 to move the left upper housing 488 upwardly so as to remove the first and second probes 492, 512 from the suction canister 14B. The holding bracket 466 can then be manually pivoted upwardly and the suction canister 14B removed from the cradle 420 of the cleaning station 400. If the right suction canister 14A is properly positioned in the right cradle 416 with the holding bracket 464 properly positioned, the controller 472 will initiate the automatic draining and cleaning cycle for the right suction canister 14A.

To prepare a drained and cleaned suction canister 14 for another use in collecting bodily fluid, the used cover 22 is removed and discarded, preferably into the waste container 452 of the cleaning station 400. A clean cover is put in place on the suction canister receptacle 18. Used covers and clean covers can be visually distinguished because the used covers do not have the seal 280 in place on the cartridge 188 and because the used covers have punched out cleaning port covers 70.

We claim:

1. A medical apparatus comprising:
   a suction canister including a suction port for communication with a vacuum source, a patient port for communication with a patient, a chamber for holding bodily fluid drained from a patient, an opening, and a rigid member occluding said opening; and
   a station operable to drain the bodily fluid from said chamber, said station including a support area for removably supporting said canister and a probe adapted to remove said member from said opening to enable said probe to communicate with said chamber and adapted to supply a fluid to said chamber.

2. The medical apparatus of claim 1 wherein said fluid is water.

3. The medical apparatus of claim 1 wherein said canister includes a lid and wherein said suction port, patient port and opening are on said lid.

4. The medical apparatus of claim 1 wherein said member is a cover and said opening is a port.

5. The medical apparatus of claim 1 wherein said probe is adapted to remove bodily fluid from said chamber.

6. The medical apparatus of claim 1 wherein said station is actuable to non-manually actuate said probe to remove said member from said opening.

7. A medical apparatus comprising:
   a suction canister including a cover and a container for holding fluid drained from a patient, said cover having therein a suction port for communication with a vacuum source, a patient port for communication with a patient, a cleaning port, and a member occluding said cleaning port; and a station operable to drain the fluid from said chamber, said station including a support area for removably supporting said canister and a probe adapted to remove said member from said cleaning port to enable said probe to communicate with the interior of said container.

8. The medical apparatus of claim 7 wherein said probe is adapted to supply a fluid to said canister.

9. The medical apparatus of claim 7 wherein said station is actuable to non-manually actuate said probe to remove said member from said cleaning port.

10. A medical apparatus comprising:

a suction canister including a suction port for communication with a vacuum source, a patient port for communication with a patient, a chamber for holding bodily fluid drained from a patient, a cleaning port, and a member occluding said cleaning port; and a station operable to drain the bodily fluid from said chamber, said station including a probe insertable into said chamber via removal of said member from said cleaning port by punching out said member from said cleaning port.

11. A medical apparatus comprising:

a suction canister for containing body fluids, said canister having therein an opening, a plug removably positioned in said opening, a patient port for communicating with a patient, and a vacuum port for communicating with a vacuum source; and a cleaning station including a probe actuable to remove said plug from said opening and thereby be insertable into said canister.

12. The medical apparatus of claim 11 wherein said suction canister has an open upper end, and further comprising a lid closing said upper end, said lid having therein said opening.

13. The medical apparatus of claim 12 wherein said plug is a weakened portion of said lid.

14. The medical apparatus of claim 12 wherein said lid has thereon said patient port and said vacuum port.

15. The medical apparatus of claim 11 wherein said probe is adapted to provide a fluid to said canister.

16. The medical apparatus of claim 11 wherein said probe is adapted to drain the body fluids from said canister.

17. The medical apparatus of claim 11 wherein said plug is a cover over said opening.

18. The medical apparatus of claim 11 wherein said probe is actuable to remove said plug through the application of a downward force.

19. The medical apparatus of claim 11 wherein said probe directly contacts said plug.

20. The medical apparatus of claim 11 wherein said cleaning station automatically actuates said probe to remove said plug.

21. A medical apparatus comprising:

a suction canister including a suction port coupleable to a vacuum source, a patient port coupleable to a patient, a bodily fluid drainage receptacle, a passageway, and a seal occluding said passageway; and a drainage station, said drainage station including a suction canister support cradle and a probe capable of removing said seat allowing said probe to communicate with said receptacle through said passageway and to supply a fluid to said receptacle.

22. A medical apparatus comprising:

a suction canister including a cover and a bodily fluid drainage container, said cover having therein a suction port coupleable to a vacuum source, a patient port coupleable to a patient, and a cleaning port having a cleaning port cover; and a drainage station, said station including a suction canister support cradle and a probe capable of removing said cleaning port cover allowing said probe to communicate with the interior of said container.

23. A medical apparatus comprising:

a suction canister including a suction port coupleable to a vacuum source, a patient port coupleable to a patient, a bodily fluid drainage receptacle, and a cleaning port having a cleaning port cover, and a drainage station, said drainage station including a cleaning probe insertable into said receptacle via removal of said cleaning port cover from said cleaning port by punching out said cleaning port cover from said cleaning port.

24. A medical apparatus comprising:

a suction canister for containing body fluids, said canister having therein a drainage opening, a drainage plug removably positioned in said drainage opening, a patient port coupleable to a patient, and a vacuum port coupleable to a vacuum source; and a station including a probe, said probe is adapted to be actuated to remove said plug from said drainage opening and to be inserted into said canister.

25. A medical apparatus comprising:

a suction canister including a bodily fluid receptacle, said receptacle being at least partially defined by a wall having therein an opening, a plug inserted in said opening, said plug being removable from said opening to provide communication with said receptacle, a patient port communicating with said receptacle for communication with a patient cavity, and a vacuum port communicating with a vacuum source such that application of a vacuum to said vacuum port creates a vacuum in said receptacle and thereby draws bodily fluids into said receptacle via said patient port, and a drainage station including a probe, said probe adapted to be actuated to remove said plug from said opening to provide communication with said receptacle and thereby drain the contents of said receptacle.

* * * * *